United States Patent [19]

Kang et al.

[11] Patent Number: 5,451,663

[45] Date of Patent: Sep. 19, 1995

[54] LONG WAVELENGTH CHEMICALLY REACTIVE DIPYRROMETHENEBORON DIFLUORIDE DYES AND CONJUGATES

[75] Inventors: Hee C. Kang; Richard P. Haugland, both of Eugene, Oreg.

[73] Assignee: Molecular Probes, Inc., Eugene, Oreg.

[21] Appl. No.: 45,758

[22] Filed: Apr. 8, 1993

Related U.S. Application Data

[62] Division of Ser. No. 786,767, Nov. 1, 1991, Pat. No. 5,274,113.

[51] Int. Cl.⁶ .................... C07K 17/00; C07K 16/00; C07K 14/00; C07H 19/00
[52] U.S. Cl. .................... 530/367; 530/350; 530/391.1; 530/391.3; 530/391.5; 530/402; 530/405; 536/22.1; 548/110; 548/405; 544/229; 546/13; 372/53; 372/54
[58] Field of Search ................. 372/53, 54; 530/391.1, 530/391.3, 391.5, 350, 367, 402, 405; 546/13; 536/22.1; 548/405, 110; 544/229

[56] References Cited

U.S. PATENT DOCUMENTS

| | | | |
|---|---|---|---|
| 4,774,339 | 9/1988 | Haugland et al. | 548/405 |
| 4,916,711 | 4/1990 | Boyer et al. | 372/53 |
| 5,106,951 | 4/1992 | Morgan et al. | 530/391.9 |
| 5,187,288 | 2/1993 | Kang et al. | 548/110 |
| 5,248,782 | 9/1993 | Haugland et al. | 548/110 |

OTHER PUBLICATIONS

Kalofonos et al., The Journal of Nuclear Medicine, vol. 31, No. 11, pp. 1791–1796 (1990).
Wories et al., A novel water-soluble fluorescent probe: Synthesis, luminescence and biological properties of the sodium salt of the 4-sulfonato-3,3', 5'5-tetramethyl-2,-2'-pyrromethen-1,1'-BF₂ complex, Recl. Trav. Chim. PAYSBAS 104, 288 (1985).
Pavlopoulos et al., Laser action from a tetramethylpyrromethene-BF₂ complex, App. Optics 27, 4998 (1988).
Demas et al., The Measurement of Photoluminescence Quantum Yields J. Phys. Chem 75, 991 (1971).
Kruse et al., New Methods for the Synthesis of 2-Arylpyrroles, Heterocycles 26, 3141 (1987).
Rapoport et al., 2,2'-Bipyrrole, J. Am. Chem. Soc. 84, 2178 (1962).
Bullock et al., A Synthesis of Coproporphyrin, J. Chem. Soc. 1430 (1958).
R. M. Silverstein, et al., 2-Pyrrolealdehyde, Org. Synth. Coll. vol. IV, p. 831.
Falk et al., Monatshefte fur Chemie, 110, 987 (1979).
Falk et al., Monatshefte fur Chemie, 121, 67 (1990).
Boyer et al., Laser action from 2,6,8-trisubstituted 1,3,5,7-tetramethyl-pyrromethene-BF₂ complexes: part 2, Applied Optics 30, 3788 (1991).
Waldmann, Science, vol. 252, pp. 1657–1662 (1991).
Borrebaeck, Journal of Immunological Methods, vol. 123, pp. 157–165 (1989).

Primary Examiner—Christina Y. Chan
Attorney, Agent, or Firm—Allegra J. Helfenstein; Anton E. Skaugset

[57] ABSTRACT

This invention relates to derivatives of dipyrrometheneboron difluoride fluorescent dyes that have an absorption maximum at wavelengths longer than about 525 nm, and are chemically reactive with nucleic acids, proteins, carbohydrates, and other biologically derived or synthetic chemical materials to form dye-conjugates. The dye-conjugates generally have the structure:

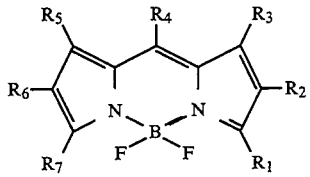

wherein at least one of the substituents $R_1$–$R_7$, covalently bonds to a specific binding pair member, and further where at least one of the substituents $R_1$–$R_7$ contains a bathochromic moiety that is heteroaryl or alkenyl. The remaining substituents, which may be the same or different, are hydrogen, halogen, alkyl (containing 1-5 carbon atoms), aryl, arylalkyl, or sulfo.

20 Claims, 4 Drawing Sheets

LONG WAVELENGTH CHEMICALLY REACTIVE DIPYRROMETHENEBORON DIFLUORIDE DYES AND CONJUGATES

This invention was made with Government support under grant number GM 37347 awarded by the National Institutes of Health. The Government has certain rights in this invention.

This is a division of application Ser. No. 07/786,767, filed Nov. 1, 1991, now U.S. Pat. No. 5,274,113.

FIELD OF THE INVENTION

This invention relates to chemically reactive fluorescent dyes that can be attached to ligands and the resulting fluorescently labeled ligands. In particular, the invention relates to chemically reactive dyes that are derivatives of dipyrrometheneboron difluoride dyes (derivatives of 4,4-difluoro-4-bora-3a,4a-diaza-s-indacene dyes) that have an absorption maximum at a wavelength longer than about 525 nm. These reactive dyes are used for the fluorescent labeling of nucleic acids, nucleotides, carbohydrates, drugs, polymers, proteins, and other biologically derived or synthetic chemical materials.

BACKGROUND OF THE INVENTION

Fluorescent dyes have many uses and are known to be particularly suitable for biological applications in which the high detectability of fluorescence is required. Fluorescent dyes are used to impart both visible color and fluorescence to other materials. Many applications utilize chemically reactive fluorescent dyes by chemically attaching the dye to reactive sites on a wide variety of materials such as cells, tissues, proteins, antibodies, enzymes, drugs, hormones, lipids, nucleotides, nucleic acids, or natural or synthetic polymers to make fluorescent conjugates. With these synthetic probes, ligands are frequently used to confer a specificity for a biochemical reaction that is to be observed and the fluorescent dye provides the means of detection or quantitation of the interaction.

Fluorescence useful for such applications is generally initiated by absorption of light from an external, relatively concentrated light source. The sensitivity of these applications is improved by having dyes that have high absorbance of the exciting light and high fluorescence quantum yield. The applications are furthermore improved by having dyes that resist photobleaching by the exciting light and that have spectral wavelengths in a range that avoids the background from contaminants that may be present in the samples. For many biological applications it is useful to have dyes whose fluorescence is not quenched by water, since most biological measurements are made in aqueous solution.

Certain lasers are particularly useful as a concentrated light source for the excitation of fluorescence. The argon laser has been the most common light source for excitation of fluorescence, with principal output at 488 nm and 514 nm. Now other lasers are increasingly used, such as helium-neon lasers that can be selected to have maximum output at either 543 nm, 594 nm, or 633 nm; the krypton laser which has significant output at 568 nm and 647 nm; and light emitting diodes which are available at this time with output commonly above 660 nm; resulting in increased demand for longer wavelength fluorescent dyes.

A number of dyes that have previously been found to be fluorescent do not have significant absorbance at desired longer excitation wavelengths. Many also have other characteristics which interfere with or limit their usefulness. For example, many known fluorescent dyes are significantly quenched in aqueous solution or are unstable during the illumination.

Dyes derived from dipyrrometheneboron difluoride have many desirable characteristics. Simple alkyl derivatives of the fluorophore 4,4-difluoro-4-bora-3a,4a-diaza-s-indacene have been described by Treibs & Kreuzer, *Difluorboryl-komplexe von di- und tripyrrylmethenen,* LIEBIGS ANNALEN CHEM. 718,208 (1968) and by Worries, Kopek, Lodder, & Lugtenburg, *A novel water-Soluble fluorescent probe: Synthesis, luminescence and biological properties of the sodium salt of the 4-sulfonato-3,3',5,5'-tetramethyl-2,2'-pyrromethen-1,1'-$BF_2$complex,* RECL. TRAV. CHIM. PAYS-BAS 104, 288 (1985) as being highly fluorescent with spectral properties that are similar to fluorescein, with maximum absorbance at about 490 to 510 nm and maximum emission at about 500 to 530 nm. U.S. Pat. No. 4,774,339 to Haugland et al. (1988) ('339 patent) describes 4,4-difluoro-4-bora-3a,4a-diaza-s-indacene (dipyrrometheneboron difluoride) dyes including hydrogen, halogen, alkyl, cycloalkyl, aryl, arylalkyl, acyl, and sulfo-substituted derivatives that contain reactive groups suitable for conjugation to biomolecules, that have good photostability, and which have fluorescein-like spectra. As described in the '339 patent, and by Pavlopoulos, et al., *Laser action from a tetramethylpyrromethene-$BF_2$complex,* APP. OPTICS 27, 4998 (1988), the emission of the alkyl derivatives of 4,4-difluoro-4-bora-3a,4a-diaza-s-indacene fluorescent dyes clearly overlaps that of fluorescein. The overlap allows the alkyl derivatives of dipyrrometheneboron difluoride to be used with the same optical equipment as used with fluorescein-based dyes without modification of the excitation sources or optical filters. As a result of having the same spectral characteristics, however, the fluorescence of the known class of alkyl-substituted 4,4-difluoro-4-bora-3a,4a-diaza-s-indacenes is not readily suitable for detection in combination with fluorescein or for use in applications where excitation by longer wavelength sources such as the helium-neon or krypton lasers or light emitting diodes is required.

Although the '339 patent discloses some dyes with an absorption maximum of greater than 525 nm (Table 5), the '339 patent is neither enabling nor prior art for the invention of the subject long wavelength reactive derivatives of dipyrrometheneboron difluoride dyes. Of the longer wavelength dyes listed, all were measured in chloroform which slightly enhances the spectral absorption and shifts the emission maxima to longer wavelength by about 10 nm (compared to methanol). The '339 patent also discloses a non-reactive dye having an absorption maximum greater than 600 nm (cmpd. 27) which has been found to have an undesirably low quantum yield and very broad absorption and emission spectral band widths.

U.S. Pat. No. 4,916,711 to Boyer, et al. (1990) ('711 patent) discloses a method of using derivatives of 4,4-difluoro-4-bora-3a,4a-diaza-s-indacene dyes, in particular symmetrical alkyl and sulfonated alkyl derivatives, as laser dyes. The '711 patent also discloses a multitude of possible alternatives for substituents of the basic tricyclic structure which can be used for the patented method. The '711 patent, however, is neither enabling nor prior art for the invention of long wavelength reactive derivatives of dipyrrometheneboron difluoride dyes. The dyes described in the '711 patent are not reactive dyes. In addition, the '711 patent neither recognizes nor recites the effect or advantage of substituents that enhance the long wavelength fluorescence properties of such dyes.

Inventors Kang and Haugland have filed two copending applications on long wavelength dyes that are non-reactive: HETEROARYL-SUBSTITUTED DIPYRROMETHENEBORON DIFLUORIDE DYES AND THEIR SYNTHESIS (Ser. No. 07/629,596, filed Dec. 18, 1990 now U.S. Pat. No. 5,248,782) and ETHENYL-SUBSTITUTED DIPYRROMETHENEBORON DIFLUORIDE DYES AND THEIR SYNTHESIS (Ser. No. 07/704,287, filed May. 22, 1991 now U.S. Pat. No. 5,187,288). In addition, other materials incorporating long wavelength dipyrrometheneboron difluoride dyes have been disclosed in co-pending applications: FLUORESCENT FATTY ACIDS DERIVED FROM DIPYRROMETHENEBORON DIFLUORIDE DYES (Ser. No. 07/654,881, filed Feb. 13, 1991 by Haugland & Kang now U.S. Pat. No. 5,338,854) and DIPYRROMETHENEBORON DIFLUORIDE LABELED FLUORESCENT MICROPARTICLES (Ser. No. 07/629,466, filed Dec. 18, 1990 by Brinkley, Haugland & Kang, pending). None of the long wavelength dipyrrometheneboron difluoride dyes described in the references are the chemically reactive dyes of this invention.

The novel dyes described in this invention contain one or more substituent groups coupled to the 4,4-difluoro-4-bora-3a,4a-diaza-s-indacene ("BDI") fluorophore resulting in significant absorbance and fluorescence at desired longer wavelengths. The dyes of this invention also have the chemical reactivity necessary for conjugation to the reactive sites commonly found in biomolecules, drugs, and natural and synthetic polymers. The reactive dyes of this invention are combined with a variety of materials to form novel dye conjugates. The novel dye conjugates are desirable for use in combination with conjugates formed from other fluorescent dyes such as fluorescein or alkyl-substituted 4,4-difluoro-4-bora-3a,4a-diaza-s-indacene dyes in that the fluorophore of the novel conjugates can be both selectively excited and detected because of their spectral shift to longer wavelengths, particularly an absorption maximum at greater than 525 nm and an emission maximum at greater than 550 nm. The new reactive dyes have the advantage over other dyes that absorb at these wavelengths, of being electrically neutral, photostable and being, in most cases, highly fluorescent in both organic and aqueous solution with relatively narrow absorption and emission spectra.

SUMMARY OF THE INVENTION AND DESCRIPTION OF PREFERRED EMBODIMENTS

Figure 1:
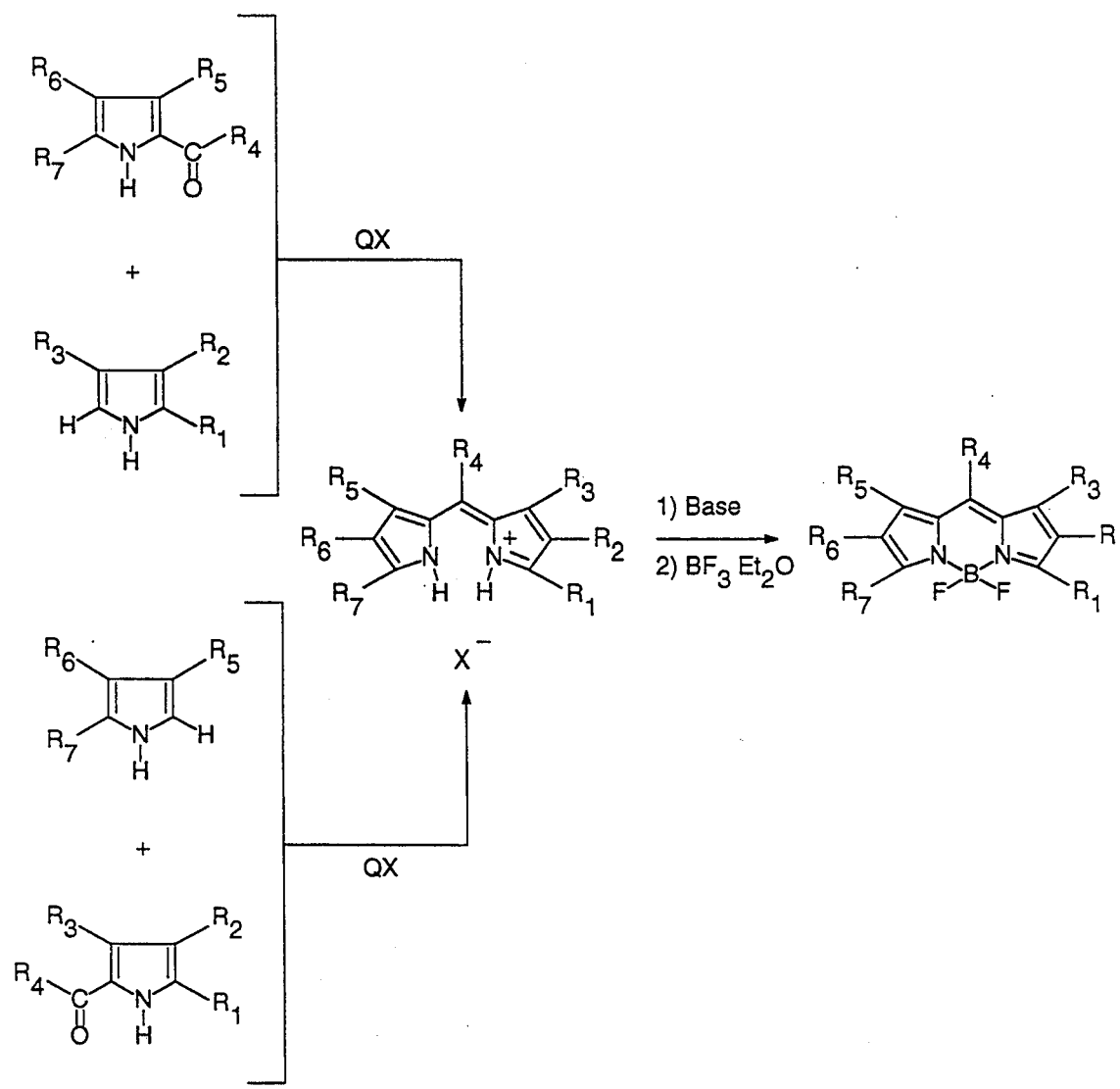
FIG. 1 is a general reaction scheme for synthesis of long wavelength reactive BDI dyes. The general method consists of a formation of pyrromethene intermediates followed by cyclization with boron trifluoride in the presence of base to give substituted dipyrrometheneboron difluoride dyes.

This invention describes novel fluorescent dyes that are reactive derivatives of the 4,4-difluoro-4-bora-3a,4a-diaza-s-indacene ("BDI") fluorophore that can be chemically reacted to bond with the reactive sites present in many materials to form novel fluorescent conjugates.

The BDI dyes generally have the structure of formula I:

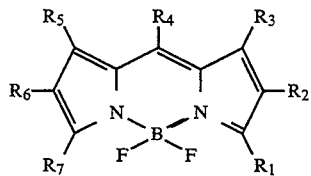

At least one of the substituents $R_1$–$R_7$ on the BDI fluorophore, is -$L_mG$ where G is a reactive functional group that allows the BDI fluorophore to be coupled to other synthetic or natural molecules. Preferably there are one or two reactive functional groups on the fluorophore; more preferably only one reactive functional group. The most common reactive functional groups are carboxylic acids and derivatives thereof including succinimidyl esters, acyl azides, anhydrides, and acid halides. Other reactive groups include acrylamides, alcohols, aldehydes, amines, azides, imido esters, sulfonate esters, haloacetamides, alkyl and aryl halides, sulfonyl halides, hydrazines, isocyanates, isothiocyanates, and maleimides. Table 1 lists common reactive functional groups and the reactive sites with which they most commonly react. The tabulation is not all inclusive since with the appropriate choice of solvent, temperature and catalysts, other functional groups can be made to react.

TABLE 1

| REACTIVE GROUPS | REACTIVE SITES |
|---|---|
| acrylamides | olefins |
| acyl azides | amines, thiols |
| alcohols | acid derivatives |
| aldehydes | amines, alcohols |
| amines | carboxylic acids, halides, aldehydes and ketones |
| anhydrides | amines, alcohols |
| azides | photoaffinity reagents |
| carbonyl halides | amines, alcohols, phenols, thiol |
| halides | alcohols, amines, thiols, carboxylic acids |
| haloacetamides | thiols, imidazoles, phenols, amines |
| hydrazines | aldehydes, ketones, acid derivatives |
| imido esters | amines |
| isocyanates | amines, thiols, alcohols, phenols |
| isothiocyanates | amines, thiols, phenols |
| maleimides | thiols, amines |
| succinimidyl esters | amines, thiols |
| sulfonyl chlorides | amines, phenols, alcohols |
| sulfonyl fluorides | active sites of esterases |

The reactive functional group is directly attached to the BDI fluorophore or is attached through a spacer $-L_m-$, where $m=0$ or 1. When the reactive functional group is directly attached to the BDI fluorophore, $m=0$ (L is absent). The spacer L is a substituted or unsubstituted alkyl (containing 1-5 carbons) or aryl group. Alternatively, L is a linking bathochromic moiety i.e. a bathochromic moiety that links the fluorophore and a reactive functional group such that the reactive functional group is a substituent on the linking bathochromic moiety. Preferably L, when present, is a straight chain unsubstituted alkyl group that contains 1-4 carbons, an unsubstituted phenyl group, or a linking bathochromic moiety.

At least one of the substituents $R_1-R_7$ contains a bathochromic moiety. The inclusion of a bathochromic moiety in any substituent shifts the fluorescence of the compound toward the red part of the spectrum and gives the fluorophore an absorption maximum of greater than about 525 nm. Typically the bathochromic moiety also gives the fluorophore an emission maximum greater than about 550 nm. Typically, the bathochromic moiety is an unsaturated organic group such as a substituted or unsubstituted ethenyl, dienyl, trienyl or heteroaryl group.

A bathochromic moiety may be present as a substituent separate from the reactive functional group (separate bathochromic moiety). At least one, and as many as six, of the substituents, can be separate bathochromic moieties any of which may be the same or different. A bathochromic moiety may also or alternatively be included in the spacer (L) connecting the reactive functional group to the BDI fluorophore (linking bathochromic moiety). One or more bathochromic moieties may be included only as linking moieties, or only separately, or combinations thereof, but a bathochromic moiety must be included in at least one of the substituents $R_1-R_7$. With seven substituent locations, there may be as many as seven bathochromic moieties, some or all of which may each be the same or different. Where the dye compound contains seven bathochromic moieties, at least one bathochromic moiety and as many a seven contain(s) a reactive functional group. Preferably there are no more than four bathochromic moieties included in the substituents $R_1-R_7$, some or all of which may contain reactive functional groups as substituents. Typically, because of the symmetry, at least one of the groups $R_1$, $R_2$, $R_3$ or $R_4$ contains a bathochromic moiety, which may contain a reactive functional group as a substituent. For ease of synthesis, the bathochromic moiety is preferably present as a substituent separate from the reactive group. In either case, the bathochromic moiety is directly attached to the BDI fluorophore by a covalent bond.

In one embodiment of the invention, there is a single bathochromic moiety that is heteroaryl. The term heteroaryl, as used throughout this document, means an aromatic heterocyclic substituent. When a heteroaryl group is present as a substituent, it is an aromatic heterocyclic moiety that contains at least one and as many as three hetero atom (a non-carbon atom forming the ring structure) that is N, O, or S. The heteroaryl group can contain one, two, or three hetero atoms. The heteroaryl group can be a single ring structure or a fused two- or three-ring structure. A ring can be a 5- or 6- membered ring. Examples of heteroaryl substituents are pyrrole, thiophene, or furan (single ring, single hetero atom), or oxazole, isoxazole, oxadiazole, or imidazole (single ring, multiple hetero atoms). Alternatively, the heteroaryl group is a multi-ring structure containing one or more hetero atoms; for example, the heteroaryl substituent is benzoxazole, benzothiazole, or benzimidazole (multi-ring, multiple hetero atoms), or benzofuran or indole (multi-ring, single hetero atom). The term heteroaryl includes substituted derivatives of the heteroaryl substituents, such as alkyl-, aryl-, arylalkyl- or heteroaryl-substituted pyrrolyl, furyl or thienyl. The bathochromic heteroaryl group may also contain a reactive functional group as a substituent.

In another embodiment of the invention, the single bathochromic moiety is an alkenyl group. Preferably the alkenyl group is ethenyl, dienyl or trienyl. The alkenyl group is unsubstituted or contains substituents, which may be the same or different that are hydrogen, halogen, alkyl (containing 1-5 carbon atoms), cyano, carboxylate ester, carboxamide, aryl or heteroaryl, or polyethenyl to form a conjugated dienyl or trienyl substituent, which in turn may be substituted with substituents, which may be the same or different, that are hydrogen, halogen, alkyl (containing 1-5 carbon atoms), cyano, ester, amide, aryl or heteroaryl groups. The bathochromic alkenyl group may also contain a reactive functional group as a substituent.

In yet another embodiment of the invention, the fluorophore has 2-4 bathochromic substituents, which may be the same or different, that are substituted or unsubstituted ethenyl, dienyl, trienyl, or heteroaryl groups. One or two of the bathochromic substituents may contain reactive functional groups, which may be the same or different, as substituents.

The remainder of the substituents $R_1-R_7$ that are neither reactive functional groups nor bathochromic substituents, which remaining substituents may be the same or different, are hydrogen, halogen, cycloalkyl or alkyl (containing 1-5 carbons), aryl, arylalkyl (the alkyl portions of which contain 1-5 carbon atoms), or sulfo, alone or in combination, as long as they do not destroy the reactivity of the dyes. Preferably, the remaining substituents are hydrogen.

Preferred aryl groups in any of the described substituents are phenyl, 1-naphthyl, 2-naphthyl, 1-pyrenyl, 9-anthryl, and their alkoxy substituted derivatives wherein the alkyl portions of such derivatives have less than 5 carbon atoms. Any aryl or heteroaryl group in any substituent may be further substituted one or more times by alkyl; or alkoxy groups, the alkyl portions of which have less than 5 carbon atoms; or combinations thereof. Any alkyl group in any substituent may be further substituted by an ester or amide substituent.

Table 2 contains a sample of representative long wavelength reactive dyes and their key precursors. The examples are preferred, representative compounds only and are not intended to be exclusive.

TABLE 2

| Compound | $R_1$ | $R_2$ | $R_3$ | $R_4$ | $R_5$ | $R_7$ |
|---|---|---|---|---|---|---|
| 1 | $(CH_2)_2CO_2CH_3$ | H | H | H | H | THI* |
| 2 | $(CH_2)_2CO_2H$ | H | H | H | H | THI* |
| 3 | $(CH_2)_2CO_2Succ*$ | H | H | H | H | THI* |

TABLE 2-continued

| Compound | $R_1$ | $R_2$ | $R_3$ | $R_4$ | $R_5$ | $R_7$ |
|---|---|---|---|---|---|---|
| 4 | $(CH_2)_2C(=O)NHNH_2$ | H | H | H | H | THI* |
| 5 | $(CH_2)_2CO_2CH_3$ | H | H | H | H | FUR* |
| 6 | $(CH_2)_2CO_2H$ | H | H | H | H | FUR* |
| 7 | $(CH_2)_2CO_2CH_3$ | H | H | H | H | PYR* |
| 8 | $(CH_2)_2CO_2H$ | H | H | H | H | PYR* |
| 9 | $(CH_2)_2CO_2Succ$ | H | H | H | H | PYR* |
| 10 | $CH_3$ | $(CH_2)_2-CO_2-CH_3$ | $CH_3$ | H | H | PYR* |
| 11 | $CH_3$ | $(CH_2)_2-CO_2H$ | $CH_3$ | H | H | PYR* |
| 12 | THI* | H | H | $(CH_2)_2-CO_2CH_3$ | $CH_3$ | $CH_3$ |
| 13 | THI* | H | H | $(CH_2)_2-CO_2$ | $CH_3$ | $CH_3$ |
| 14 | (p)-$C_6H_4$—$OCH_2CO_2CH_3$ | H | H | H | H | THI* |
| 15 | (p)-$C_6H_4$—$OCH_2CO_2H$ | H | H | H | H | THI* |
| 16 | (p)-$C_6H_4$—$OCH_2CO_2Succ$* | H | H | H | H | THI* |
| 17 | (p)-$C_6H_4$—$OCH_2CO_2CH_3$ | H | H | H | H | FUR* |
| 18 | (p)-$C_6H_4$—$OCH_2CO_2H$ | H | H | H | H | FUR* |
| 19 | (p)-$C_6H_4$—$OCH_2CO_2CH_3$ | H | H | H | H | PYR* |
| 20 | (p)-$C_6H_4$—$OCH_2CO_2H$ | H | H | H | H | PYR* |
| 21 | (p)-$C_6H_4$—$OCH_2CO_2Succ$* | H | H | H | H | PYR* |
| 22 | (p)-$C_6H_4$—$OCH_2CO_2CH_3$ | H | H | H | H | ST* |
| 23 | MCMST* | H | H | H | H | ST* |
| 24 | CMST* | H | H | H | H | ST* |
| 25 | (p)-$C_6H_4$—$OCH_2CO_2CH_3$ | H | H | H | H | PHBD* |
| 26 | (p)-$C_6H_4$—$OCH_2CO_2H$ | H | H | H | H | PHBD* |
| 27 | $(CH_2)_2CO_2CH_3$ | H | H | H | H | PHBD* |
| 28 | $(CH_2)_2CO_2H$ | H | H | H | H | PHBD* |
| 29 | $(CH_2)_2CO_2Succ$* | H | H | H | H | PHBD* |
| 30 | (E)-CH=$CHCO_2CH_3$ | H | H | H | $CH_3$ | $CH_3$ |
| 31 | (E)-CH=$CHCO_2H$ | H | H | H | $CH_3$ | $CH_3$ |
| 32 | (E)-CH=$CHCO_2Succ$* | H | H | H | $CH_3$ | $CH_3$ |
| 33 | (E)-CH=$CHCO_2CH_3$ | H | H | H | $C_6H_5$ | $C_6H_5$ |
| 34 | (E)-CH=$CHCO_2H$ | H | H | H | $C_6H_5$ | $C_6H_5$ |
| 35 | (E)-CH=$CHCO_2Succ$* | H | H | H | $C_6H_5$ | $C_6H_5$ |
| 36 | CEMOXET* | H | H | H | $CH_3$ | $CH_3$ |
| 37 | CMMOXET* | H | H | H | $CH_3$ | $CH_3$ |
| 38 | $(CH_2)_2CO_2CH_3$ | H | H | H | H | (E)-CH=$CHCH_3$ |
| 39 | (p)-$C_6H_4$—$OCH_2CO_2CH_3$ | H | H | H | H | (E)-CH=$CHCH_3$ |
| 40 | (p)-$C_6H_4$—$OCH_2CO_2H$ | H | H | H | H | (E)-CH=$CHCH_3$ |
| 41 | MCST* | H | H | H | $CH_3$ | $CH_3$ |
| 42 | HMPHET* | H | H | H | $CH_3$ | $CH_3$ |
| 43 | CMPHET* | H | H | H | $CH_3$ | $CH_3$ |
| 44 | $(CH_2)_2CO_2CH_3$ | H | H | H | H | NAET* |
| 45 | $(CH_2)_2CO_2CH_3$ | H | H | H | H | ST* |
| 46 | $(CH_2)_2CO_2H$ | H | H | H | H | ST* |
| 47 | $(CH_2)_2CO_2Succ$* | H | H | H | H | ST* |
| 48 | $(CH_2)_2C(=O)NH(CH_2)_2-NH_2$ | H | H | H | H | ST* |
| 49 | $(CH_2)_2C(=O)NH(CH_2)_2-$NH$-$C($=$O)$CH_2$I | H | H | H | H | ST* |
| 50 | $(CH_2)_2C(=O)NH(CH_2)_2-$NH$-$C($=$O)$CH_2$-Maleim* | H | H | H | H | ST |
| 51 | $(CH_2)_2C(=O)NH(CH_2)_2-$NH$-$C($=$O)$-(p)-$C_6H_4$—CHO | H | H | H | H | ST* |
| 52 | $(CH_2)_2C(=O)NH(CH_2)_2-$NH$-$C($=$O)$-(p)-$C_6H_4$—$N_3$ | H | H | H | H | ST* |
| 53 | $(CH_2)_2C(=O)NH(CH_2)_2-$NH$-$C($=$O)$-CH=$CH_2$ | H | H | H | H | ST* |
| 54 | $(CH_2)_2C(=O)NH(CH_2)_2-$N=C=S | H | H | H | H | ST* |
| 55 | $(CH_2)_2C(=O)-O-C(=O)-O-CH_2CH_3$ | H | H | H | H | THI* |
| 56 | $(CH_2)_2C(=O)-N_3$ | H | H | H | H | THI* |
| 57 | $(CH_2)_2C(=O)-F$ | H | H | H | H | THI* |
| 58 | $(CH_2)_2C(=O)NH(CH_2)_3-CH_3$ | H | H | H | H | THI* |
| 59 | ST | $SO_3Na$ | H | H | $SO_3Na$ | ST |
| 60 | ST | $SO_2Cl$ | H | H | $SO_2Cl$ | ST |
| 61 | $(CH_2)_2C(=O)NH(CH_2)_2-NH_2$ | H | H | H | H | THI* |
| 62 | $(CH_2)_2C(=O)NH(CH_2)_2-NHC(=O)CH_2I$ | H | H | H | H | THI* |
| R‡ | $(CH_2)_2CO_2H$ | H | H | H | $CH_3$ | $CH_3$ |

† Substituents $R_1$-$R_7$ correspond to the formula in the text above; $R_6$ is hydrogen in all of the structures listed in Table 2.
*The names and chemical structures of abbreviations used in this table are shown immediately below.
‡ Alkyl-substituted reactive dipyrromethenebboron difluoride dye, included for comparison.

THI: 2-thienyl, 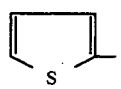    FUR: 2-furyl, 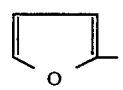    PYR: 2-pyrrolyl, 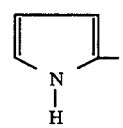

ST: (E)-2-phenylethen-1-yl, 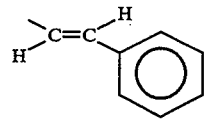

PHBD: (E,E)-4-phenyl-1,3-butadien-1-yl, 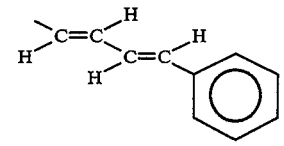

MCMST: (E)-2-[4-(methoxycarbonylmethoxy)phenyl]ethen-1-yl, 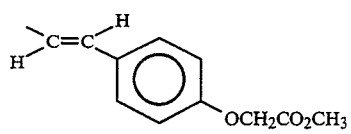

CMST: (E)-2-[4-(carboxymethoxy)phenyl]ethen-1-yl, 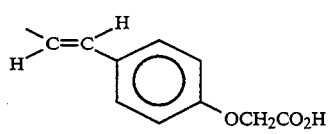

MCST: (E)-2-[4-(methoxycarbonyl)phenyl]ethen-1-yl, 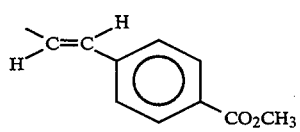

CEMOXET: (E)-2-(5-carboethoxy-4-methyl-2-oxazolyl)ethen-1-yl, 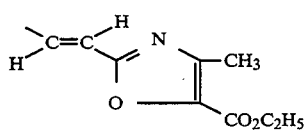

CMMOXET: (E)-2-(5-carbomethoxy-4-methyl-2-oxazolyl)ethen-1-yl, 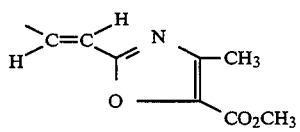

HMPHET: (E)-2-[4-(hydroxymethyl)phenyl]ethen-1-yl, 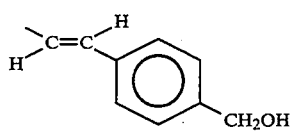

CMPHET: (E)-2-[4-(chloromethyl)phenyl]ethen-1-yl, 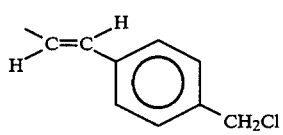

NAET: (E)-2-(1-naphthyl)ethen-1-yl, 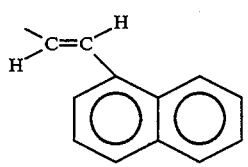

Succ: succinimidyl, 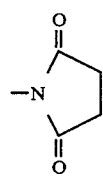    Maleim: maleimidyl, 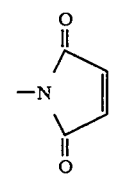

Table 3 describes physical properties of selected dyes from Table 2.

| Compound | mp | Abs | Em | | Solvent |
|---|---|---|---|---|---|
| 2 | 170–171 | 559.6 | 568 | 0.29 | C |
| 3 | 70–72 | 559.4 | 568 | 0.65 | B |
| 4 | 164–166 | 557.2 | 569 | 0.36 | C |
| 6 | 139–141 | 560.8 | 570 | 0.24 | C |
| 8 | 158–160 | 578.2 | 589 | 0.37 | C |
| 11 | 200 dec | 585.4 | 599 | 0.29 | C |
| 13 | 191–193 | 546.0 | 564 | 0.19 | C |
| 15 | 210 dec | 591.0 | 618 | 0.32 | D |
| 16 | 188–189 | 588.2 | 617 | 0.40 | C |
| 20 | 190 dec | 609.0 | 640 | 0.31 | D |
| 24 | 175 dec | 637.4 | 652 | 0.48 | D |
| 26 | 188 dec | 621.2 | 643 | 0.34 | D |
| 28 | 197–199 | 582.4 | 590 | 0.31 | C |
| 29 | 125–126 | 581.8 | 591 | 0.54 | B |
| 31 | 160 dec | 535.2 | 544 | 0.17 | C |
| 32 | 203–206 | 538.0 | 549 | 0.48 | B |
| 34 | 163 dec | 574.0 | 589 | 0.35 | C |
| 35 | 195–196 | 580.6 | 598 | 0.71 | C |
| 37 | 252–253 | 561.4 | 570 | 0.15 | A |
| 40 | 210 dec | 571.4 | 592 | 0.22 | D |
| 42 | 168–170 | 560.4 | 571 | 0.29 | B |
| 43 | 193–195 | 560.0 | 570 | 0.83 | A |
| 44 | 136–138 | 569.6 | 579 | 0.46 | A |
| 45 | 145–146 | 563.2 | 569 | 0.22 | A |
| 46 | 195–197 | 564.4 | 570 | 0.32 | C |
| 47 | 204–205 | 563.4 | 570 | 0.76 | C |
| 48 | 120 dec | 564.4 | 570 | 0.06 | D |
| 49 | 188–189 | 564.4 | 570 | 0.50 | C |
| 50 | 104 dec | 564.4 | 570 | 0.33 | C |
| 51 | 190–192 | 564.4 | 571 | 0.34 | C |
| 52 | 152–153 | 565.0 | 571 | 0.49 | C |
| 53 | 178–180 | 564.2 | 570 | 0.39 | C |
| 54 | 140–141 | 564.4 | 570 | 0.59 | C |
| 56 | 70–80 | 558.6 | 568 | 0.53 | C |
| 58 | 126–127 | 559.0 | 569 | 0.58 | C |
| 59 | 130 dec | 623.2 | 635 | 0.17 | E |
| 62 | 167–168 | 559.0 | 569 | 0.37 | C |

*Absorption (Abs) and emission (Em) maxima measured in methanol.
A = Chloroform; B = 5% methanol in chloroform; C = 10% methanol in chloroform; D = 25% methanol in chloroform; E = 40% methanol in chloroform Table 4 lists the $^1$H NMR spectral data for selected dyes from Table 2.

TABLE 4

| COMPOUND | CHEMICAL SHIFT IN PPM IN CDCl$_3$ (400 MHz NMR) |
|---|---|
| 2 | 2.86(t, 2H, CH$_2$), 3.38(t, 2H, CH$_2$), 6.40(d, 1H, ArH), 6.80(d, 1H, ArH), 6.99(d, 1H, ArH), 7.04(d, 1H, ArH), 7.12(s, 1H, ArCH=), 7.17–7.20(m, 1H, ArH), 7.50(d, 1H, ArH), 8.17(d, 1H, ArH). |
| 3 | 2.84(s, 4H, 2×CH$_2$), 3.11(t, 2H, CH$_2$), 3.46(t, 2H, CH$_2$), 6.44(d, 1H, ArH), 6.81(d, 1H, ArH), 6.99(d, 1H, ArH), 7.05(d, 1H, ArH), 7.13(s, 1H, ArCH=), 7.20(t, 1H, ArH), 7.52(d, 1H, ArH), 8.19(d, 1H, ArH). |
| 4 | 2.64(t, 2H, CH$_2$), 3.35(t, 2H, CH$_2$), 3.87(bs, 2H, NH$_2$), 6.38(d, 1H, ArH), 6.81(d, 1H, ArH), 6.90(bs, 1H, NH), 6.98(d, 1H, ArH), 7.05(d, 1H, ArH), 7.13(s, 1H, ArCH=), 7.18–7.21(m, 1H, ArH), 7.51(d, 1H, ArH), 8.14(d, 1H, ArH). |
| 6 | 2.87(t, 2H, CH$_2$), 3.38(t, 2H, CH$_2$), 6.38(d, 1H, ArH), 6.61–6.63(m, 1H, ArH), 6.96(d, 1H, ArH), 6.97(d, 1H, ArH), 7.04(d, 1H, ArH), 7.10(s, 1H, ArCH=), 7.59(d, 1H, ArH), 7.69(d, 1H, ArH). |
| 8 | 2.86(t, 2H, CH$_2$), 3.35(t, 2H, CH$_2$), 6.30(d, 1H, ArH), 6.37–6.39(m, 1H, ArH), 6.84(d, 1H, ArH), 6.88(d, 1H, ArH), 6.99(s, 1H, ArCH=), 6.99–7.01(m, 1H, ArH), 7.05(d, 1H, ArH), 7.17–7.20(m, 1H, ArH). |
| 11 | 2.08(s, 3H, CH$_3$), 2.31(t, 2H, CH$_2$), 2.43(s, 3H, CH$_3$), 2.61(t, 2H, CH$_2$), 6.17–6.20(m, 1H, ArH), 6.65(d, 1H, ArH), 6.75–6.77(m, 1H, ArH), 6.84(d, 1H, ArH), 6.87(s, 1H, ArCH=), 6.93–6.95(m, 1H, ArH), 0.2(bs, 1H, NH). |
| 13 | 2.45(s, 3H, CH$_3$), 2.60(s, 3H, CH$_3$), 2.74(t, 2H, CH$_2$), 3.28(t, 2H, CH$_2$), 6.18(s, 1H, ArH), 6.74(d, 1H, ArH), 7.13–7.16(m, 1H, ArH), 7.41(d, 1H, ArH), 8.02(d, 1H, ArH). |
| 14 | 3.84(s, 3H, CH$_3$), 4.71(s, 2H, CH$_2$), 6.66(d, 1H, ArH), 6.81(d, 1H, ArH), 7.00(d, 2H, 2×ArH), 7.04(d, 1H, ArH), 7.08(d, 1H, ArH), 7.13–7.15(m, 1H, ArH), 7.16(s, 1H, ArCH=), 7.46(d, 1H, ArH), 7.96(d, 2H, 2×ArH), 8.11(d, 1H, ArH). |
| 28* | 2.68(t, 2H, CH$_2$), 3.17(t, 2H, CH$_2$), 6.47(d, 1H, ArH), 6.97(d, 1H, CH=), 7.13(d, 1H, CH=), 7.16(d, 1H, ArH), 7.18(d, 1H, ArH), 7.56(s, 1H, ArCH=), 7.61(d, 2H, 2×ArH), the remaining six protons are overlapped between 7.28 and 7.54. |
| 37 | 2.28(s, 3H, CH$_3$), 2.51(s, 3H, CH$_3$), 2.64(s, 3H, CH$_3$), 3.94(s, 3H, CH$_3$), 6.20(s, 1H, ArH), 6.83(d, 1H, ArH), 6.91(d, 1H, ArH), 7.00(d, 1H, CH=), 7.10(s, 1H, ArCH=), 8.02(d, 1H, CH=). |
| 42 | 2.26(s, 3H, CH$_3$), 2.61(s, 3H, CH$_3$), 4.71(s, 2H, CH$_2$), 6.12(s, 1H, ArH), 6.86(d, 1H, ArH), 6.95(d, 1H, ArH), 7.05(s, 1H, ArCH=), 7.27(d, 1H, CH=), 7.37(d, 2H, 2×ArH), 7.59(d, 2H, 2×ArH), 7.63(d, 1H, CH=). |
| 43 | 2.25(s, 3H, CH$_3$), 2.61(s, 3H, CH$_3$), 4.60(s, 2H, CH$_2$), 6.12(s, 1H, ArH), 6.84(d, 1H, ArH), 6.93(d, 1H, ArH), 7.05(s, 1H, ArCH=), 7.24(d, 1H, CH=), 7.38(d, 2H, 2×ArH), 7.57(d, 2H, 2×ArH), 7.63(d, 2H, 2×ArH). |
| 44 | 2.82(t, 2H, CH$_2$), 3.37(t, 2H, CH$_2$), 3.71(s, 3H, CH$_3$), 6.36(d, 1H, ArH), 6.97(d, 1H, ArH), 7.06(d, 1H, ArH), 7.09(d, 1H, ArH), 7.11(s, 1H, ArCH=), 7.77(d, 1H, CH=), 7.86–7.90(m, 2H, 2×ArH), 7.98(d, 1H, ArH), 8.18–8.23(m, 2H, 2×ArH), the remaining one olefin proton and two aromatic protons are overlapped between 7.51 and 7.59 as multiplets. |
| 45 | 2.82(t, 2H, CH$_2$), 3.37(t, 2H, CH$_2$), 3.72(s, 3H, CH$_3$), 6.34(d, 1H, ArH), 6.91(d, 1H, ArH), 6.93(d, 1H, ArH), 7.00(s, 1H, ArCH=), 7.02(d, 1H, ArH), 7.30–7.42(m, 3H, 3×ArH), 7.37(d, 1H, CH=), 7.61(d, 2H, 2×ArH), 7.66(d, 2H, CH=). |
| 46* | 2.70(t, 2H, CH$_2$), 3.17(t, 2H, CH$_2$), 6.51(d, 1H, ArH), 7.23(d, 1H, ArH), 7.24(d, 1H, ArH), 7.34(d, 1H, ArH), 7.37–7.41(m, 1H, ArH), 7.44–7.50(m, 2H, 2×ArH), 7.49(d, 1H, CH=), 7.61–7.64(m, 2H, 2×ArH), 7.63(s, 1H, ArCH=), 7.71(d, 1H, CH=). |
| 47 | 2.84(s, 4H, 2×CH$_2$), 3.31(t, 2H, CH$_2$), 3.41(t, 2H, CH$_2$), 6.41(d, 1H, ArH), 6.93(d, 1H, ArH), 6.95(d, 1H, ArH), 7.05(d, 1H, ArH), 7.09(s, 1H, ArCH=), 7.52(d, 2H, 2×ArH), 7.65(d, 1H, CH=), the remaining three aromatic protons and one olefin proton are overlapped between 7.32 and 7.43 as multiplets. |
| 48 | 2.70(t, 2H, CH$_2$), 2.71–2.76(m, 2H, CH$_2$), 3.24–3.29(m, 2H, CH$_2$), 3.35(t, 2H, CH$_2$), 6.12(bs, 1H, NH), 6.37(d, 1H, ArH), 6.93(d, 1H, ArH), 6.95(d, 1H, ArH), 7.05(d, 1H, ArH), 7.08(s, 1H, ArCH=), 7.61(d, 2H, 2×ArH), 7.65(d, 1H, CH=), the remaining three aromatic protons and one olefin proton are overlapped between 7.31 and 7.42 as multiplets. |
| 49 | 2.74(t, 2H, CH$_2$), 3.28–3.37(m, 6H, 3×CH$_2$), 3.60(s, 2H, CH$_2$), 6.38(d, 1H, ArH), 6.69–6.74(m, 1H, NH), 6.96(d, 1H, ArH), 6.98(d, 1H, ArH), 7.08(d, 1H, ArH), 7.12(s, 1H, ArCH=), 7.42(d, 2H, 2×ArH), 7.62(d, 1H, CH=), the remaining three aromatic protons and one olefin proton are overlapped between 7.33 and 7.46 as multiplets. |
| 50 | 2.25–2.34(m, 6H, 3×CH$_3$), 2.71(t, 2H, CH$_2$), 4.11(s, 2H, CH$_2$), 6.19–6.23(m, 1H, NH), 6.38(d, 1H, ArH), 6.78(s, 2H, 2×CH=), 6.89–6.91(m, 1H, NH), 6.94(d, 1H, ArH), 6.99(d, 1H, ArH), 7.07(d, 1H, ArH), 7.11(s, 1H, ArCH=), 7.61(d, 2H, 2×ArH), 7.64(d, 1H, CH=), the remaining three aromatic protons and one olefin proton are overlapped between 7.32 and 7.43 as multiplets. |
| 51 | 2.76(t, 2H, CH$_2$), 3.30–3.58(m, 6H, 3×CH$_2$), 6.25(d, 1H, ArH), 6.34–6.41(m, 1H, NH), 6.82(d, 1H, ArH), 6.94(d, 1H, ArH), 7.01(s, 1H, ArCH=), 7.03(d, 1H, ArH), 7.63(d, 1H, CH=), 7.55–7.64(m, 3H, 3×ArH), 7.83–8.00(m, 4H, 4×ArH), 9.98(S, 1H, CHO), the remaining three aromatic protons and one olefin proton are overlapped between 7.30 and 7.45 as multiplets. |
| 52 | 2.74(t, 2H, CH$_2$), 3.30–3.57(m, 6H, 3×CH$_2$), 6.22(d, 1H, ArH), 6.42–6.54(m, 1H, NH), 6.78(d, 1H, ArH), 6.88(d, 1H, ArH), 6.93(d, 2H, 2×ArH), 6.96(s, 1H, ArCH=), 6.98(d, 1H, ArH), 7.49–7.54(m, 2H, 2×ArH), 7.54(d, 1H, CH=), the remaining three aromatic protons and one olefin proton are overlapped between 7.27 and 7.34 as multiplets. |
| 53 | 2.43(t, 2H, CH$_2$), 2.58(t, 2H, CH$_2$), 3.24–3.28(m, 4H, 2×CH$_2$), 4.29–4.33(m, 2H, =CH$_2$), 5.73–5.76(m, 1H, CH=), 5.97–6.06(m, 1H, NH), 6.28–6.35(m, 1H, NH), 6.87(d, 1H, ArH), 6.90(d, 1H, ArH), 7.00(d, 1H, ArH), 7.04(s, 1H, ArCH=), 7.53(d, 2H, 2×ArH), 7.54(d, 1H, CH=). |
| 54 | 2.74(t, 2H, CH$_2$), 3.35(t, 2H, CH$_2$), 3.46(t, 2H, CH$_2$), |

TABLE 4-continued

| COMPOUND | CHEMICAL SHIFT IN PPM IN CDCl$_3$ (400 MHz NMR) |
|---|---|
| | 3.59(t, 2H, CH$_2$), 6.08(bs, 1H, NH), 6.36(d, 1H, ArH), 6.95(d, 1H, ArH), 6.98(d, 1H, ArH), 7.07(d, 1H, ArH), 7.12(s, 1H, ArCH=), 7.62(d, 2H, 2×ArH), 7.65(d, 1H, CH=), the remaining three aromatic protons and one olefin proton are overlapped between 7.32 and 7.45 as multiplets. |
| 56 | 3.32(t, 2H, CH$_2$), 3.72(t, 2H, CH$_2$), 6.43(d, 1H, ArH), 6.81(d, 1H, ArH), 7.00(d, 1H, ArH), 7.06(d, 1H, ArH), 7.14(s, 1H, ArCH=), 7.20(t, 1H, ArH), 7.52(d, 1H, ArH), 8.18(d, 1H, ArH). |
| 59* | 7.32–7.38(m, 2H, 2×ArH), 7.40–7.49(m, 4H, 4×ArH), 7.53(s, 2H, 2×ArH), 7.54(s, 1H, ArCH=), 7.70(d, 4H, 4×ArH), 7.78(d, 2H, 2×CH=), 8.48(d, 2H, 2×CH=). |
| 62 | 2.72(t, 2H, CH$_2$), 3.30–3.38(m, 6H, 3×CH$_2$), 3.58(s, 2H, CH$_2$), 6.07–6.14(m, 1H, NH), 6.41(d, 1H, ArH), 6.66–6.72(m, 1H, NH), 6.82(d, 1H, ArH), 7.01(d, 1H, ArH), 7.08(d, 1H, ArH), 7.15(s, 1H, ArCH=), 7.19–7.21(m, 1H, ArH), 7.53(d, 1H, ArH), 8.14(d, 1H, ArH). |

Compounds 28 and 46 were measured in DMSO-d$_6$ and 59 was taken in CD$_3$OD.

The additional electronic conjugation that results from incorporation of bathochromic moieties into the BDI fluorophore results in new long wavelength reactive BDI dyes that have spectral properties that are significantly shifted from those of the related alkyl-substituted fluorophores, thus permitting their use in multicolor fluorescence applications in combination with fluorescein or alkyl-substituted BDI dyes. Furthermore, this wavelength shift is usually accompanied by an increase in photostability of the long wavelength reactive BDI dyes and in most cases by an increase in the extinction coefficient of the long wavelength reactive BDI dyes relative to the alkyl-substituted BDI dyes. Table 5 lists the spectral properties of selected dyes from Table 2.

TABLE 5

| Compound | $\lambda^{Abs}_{max}$ (nm)* | $\epsilon \times 10^{-3}$ (cm$^{-1}$M$^{-1}$)* | $\lambda^{Em}_{max}$ (nm)* | Quantum Yield ($\Phi$) | Photostability |
|---|---|---|---|---|---|
| 2 | 559.2 | 86.9 | 568 | 1.00 | 0.94 |
| 8 | 578.0 | 99.2 | 589 | 0.74 | 0.96 |
| 28 | 582.2 | 158.8 | 590 | 0.81 | 0.96 |
| 46 | 564.2 | 143.2 | 570 | 0.90 | 0.92 |
| R | 505.0 | 83.8 | 512 | 1.00 | 0.71 |

+ Compound R is presented as an example of alkyl-substituted dipyrromethenebron difluoride dyes for comparison.
*Absorption (Abs) and emission (Em) maxima measured in methanol. Extinction coefficients ($\epsilon$) at their absorption maxima in methanol.
‡ Fluorescence quantum yields ($\Phi$) in methanol are measured relative to fluorescein in 0.1M NAOH ($\Phi = 0.92$). Integrated fluorescence intensities are corrected for variation of solvent refractive index. The integrated fluorescent intensity is also corrected for variation of incident excitation light intensity with wavelength by recording spectra in ratio mode relative to a rhodamine B/ethylene glycol quantum counter solution. [Demas, et al. J. PHYS. CHEM. 75, 991 (197 1)].

Retention of emission intensity after continuous illumination at absorption maxima for 30 minutes in acetonitrile. Intensity at 0 minutes = 1.00 (Example 29)

Figure 4:
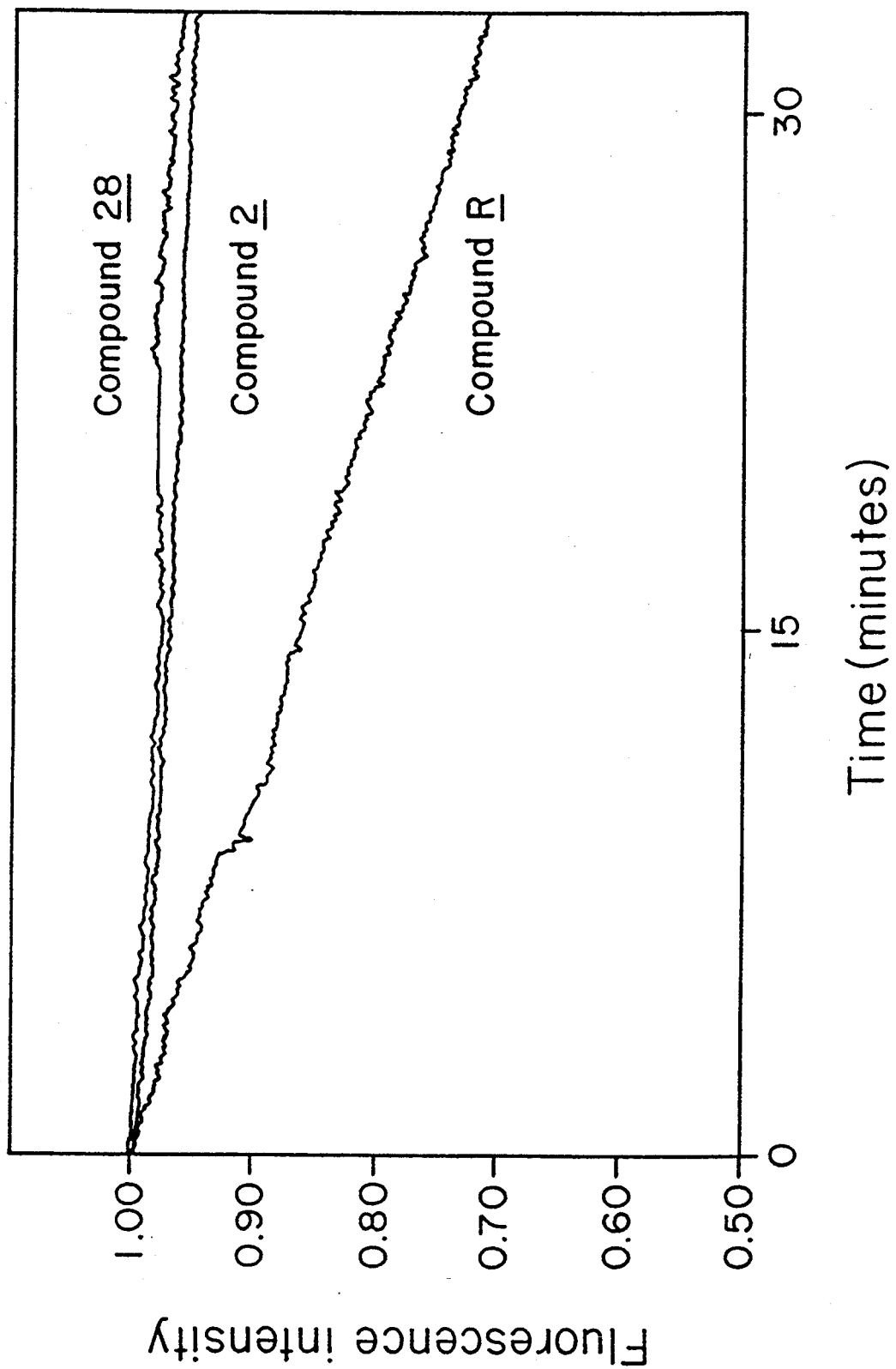
FIG. 4 is a graph showing the increased photostability of representative long wavelength reactive BDI dyes in comparison with an alkyl-substituted BDI dye, in CH3CN solution.

The novel dyes have an absorption maximum at greater than about 525 nm and, preferably, an emission maximum at greater than about 550 nm (see Table 3). These spectral properties distinguish the long wavelength reactive BDI dyes from the related alkyl-substituted BDI dyes. As indicated in Table 5 below, the absorption and emission spectra of the new reactive BDI dyes are shifted to significantly longer wavelengths as compared to the alkyl-substituted dyes. The long wavelength reactive BDI dyes also demonstrate improved photostability (Table 5, FIG. 4) relative to the alkyl-substituted dyes; with high extinction coefficients, generally greater than 80,000 cm$^{-1}$M$^{-1}$ (Table 5). The dyes of this invention also have a substantial quantum yield, i.e. greater than 0.1 as measured in

TABLE 5-continued methanol (Table 5), which distinguishes these dyes from previously disclosed BDI derivatives having an absorption maximum greater than about 525 nm.

Figure 2:
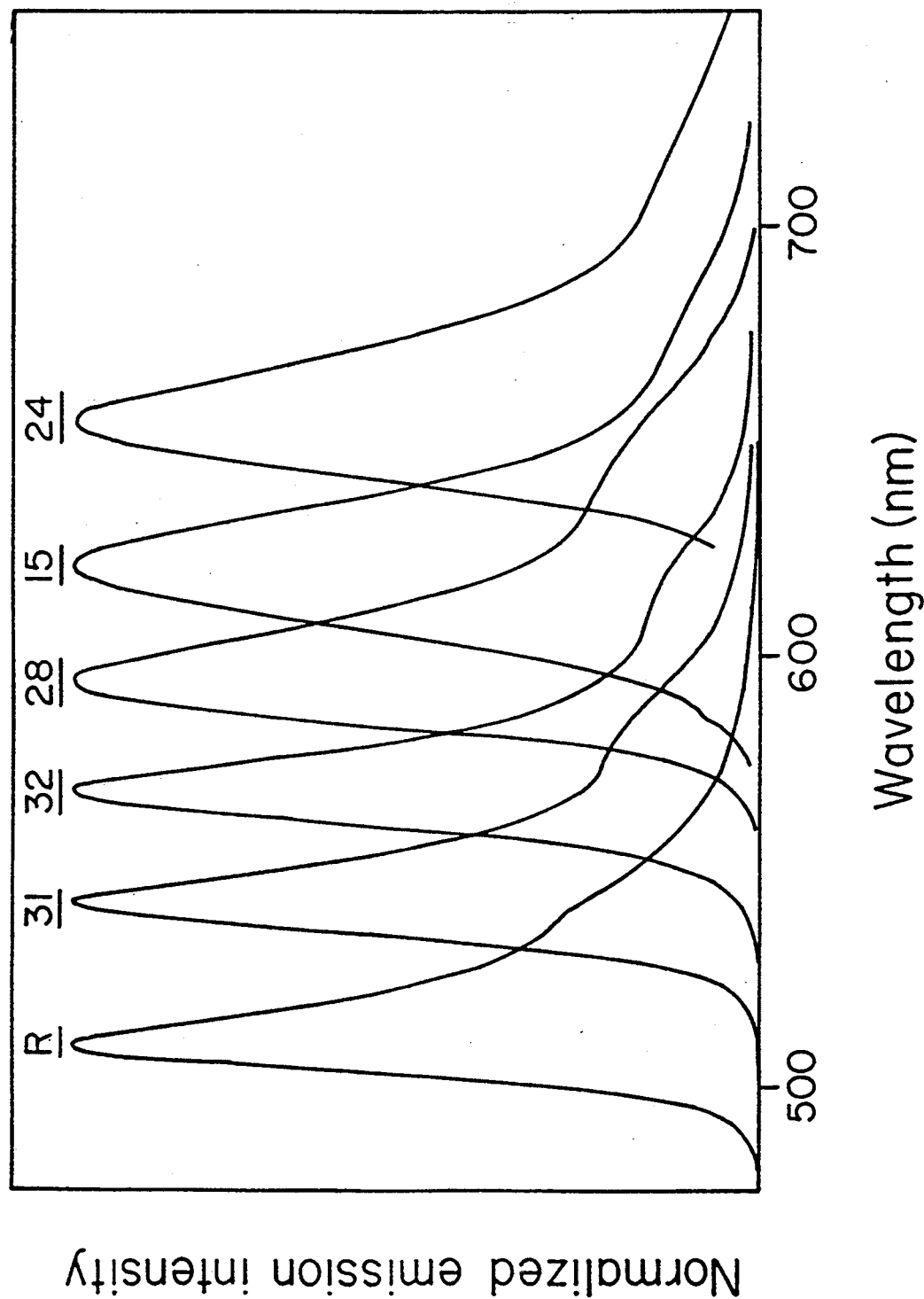
FIG. 2 is a graph of the relative spectral separations of selected examples of long wavelength reactive BDI dyes in comparison with an alkyl-substituted BDI dye, in pH 7 phosphate buffer solution.
Figure 3:
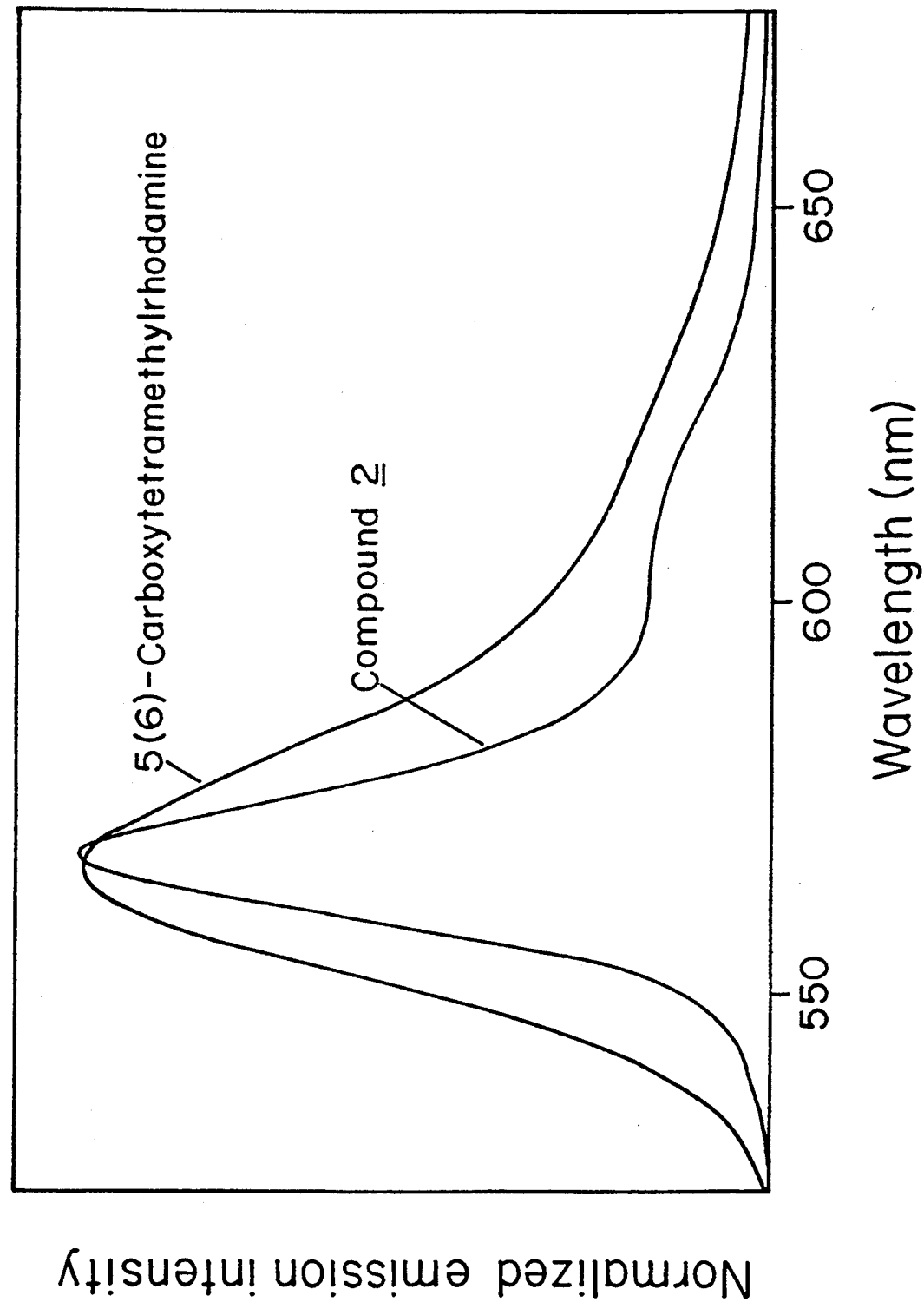
FIG. 3 is a graph showing the relatively narrow emission band width of a selected long wavelength reactive BDI dye in comparison with another known dye emitting at the same wavelength (in methanol, excited at 540 nm).

Of further significance is the characteristic that the emission spectra of appropriate combinations of the dyes can be readily resolved (FIG. 2). This relatively high degree of spectral resolution is partly the result of the unusually narrow emission band width of most BDI dyes (including the subject dyes) relative to that of other important fluorophores in common use such as a tetramethylrhodamine derivative (FIG. 3). Furthermore, the fluorescence of the long wavelength reactive BDI dyes is not usually quenched in aqueous solution. This general insensitivity of the dye to the environment of use increases the utility of these dyes in their applications.

The general scheme for the synthesis of new long wavelength BDI dyes that can be modified to have the desired chemical reactivity falling within the scope of this invention is illustrated in FIG. 1. Suitable substituents $R_1$ to $R_7$ (FIG. 1) on the pyrrole intermediates include, but are not limited to, hydrogen, alkyl, cycloalkyl, aryl, arylalkyl, heteroaryl and alkenyl.

The general method consists of an acid catalyzed condensation of a 2-acylpyrrole or appropriately substituted 2-acylpyrrole with pyrrole or substituted pyrrole having a hydrogen on the 2-position used in approximately stoichiometric proportions to give a pyrromethene intermediate. In general, there are two alternative routes whose choice depends primarily on the availability or ease of synthesis of the 2-acylpyrrole reactants. Suitable acids (QX) include, but are not limited to, hydrogen halides, metal salts typically used in Friedel-Craft reactions such as zinc halides, and non-metallic, electron deficient Lewis acids such as boron halides, halides of sulfur acids and phosphorous oxychloride in that such acids contain elements or groups of elements capable of forming an anionic counterion. Preferred is phosphorous oxychloride, since its use results in moderate to good yields of pyrromethene intermediates. In some cases it may be practical to use boron trifluoride both as the acid component and to complete formation of the BDI dye in a "one pot reaction".

Cyclization of the heterocyclic ring with formation of the BDI dye is completed by addition of boron trifluoride in combination with a suitable base. Boron trifluoride is preferably used as one of its ether complexes due to the ease of handling of these complexes rather than the gaseous reagent. Suitable bases include, but are not limited to, trimethylamine, triethylamine, N,N-diisopropylethylamine, N,N,N',N'-tetramethylethylenediamine, 1,8-bis(dimethylamino)naphthalene, diazabicyclooctane, diazabicycloundecene, 4-dimethylaminopyridine, 4-pyrrolidinopyridine and other similar bases.

Once prepared, the long wavelength reactive BDI dyes may be further modified by sulfonation, nitration, alkylation, acylation, halogenation and other reactions by methods known in the art, such as described in Example 24 and by U.S. Pat. No. 4,916,711 to Boyer, et al. (1990) (incorporated by reference); Worries, et al., *A novel water-soluble fluorescent probe: Synthesis, luminescence and biological properties of the sodium salt of the 4-sulfonato-3,3', 5,5'-tetramethyl-2,2'-pyrromethen-1,1'-*

$BF_2 complex$, RECL. TRAV. CHIM. PAYS-BAS 104, 288 (1985).

The resulting products are generally soluble in organic solvents. Aqueous solubility can be obtained by adding appropriate water solubilization groups that include sulfonates, carboxylates, ammonium and hydroxyl residues to the dyes. In most cases, the solid dyes are easily purified by techniques of chromatography and/or crystallization from a suitable solvent. The chemical structures of representative examples of long wavelength reactive BDI dyes have been confirmed by nuclear magnetic resonance spectroscopy (Table 4).

Once synthesized, the new long wavelength chemically reactive BDI dyes can be used to fluorescently label a wide variety of other materials, including cells, tissues, carbohydrates, drugs, lipids, nucleic acids, nucleotides, polymers, oligonucleotides, proteins, toxins, viruses, vitamins, and other biologically derived or synthetic chemical materials. The novel BDI dyes are particularly useful for the fluorescent labeling of members of specific binding pairs (sbp) to form dye conjugates which can be used to detect biological interactions. The sbp member can be a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; lipids; polysaccharides and carbohydrates; and a variety of drugs, including therapeutic drugs and drugs of abuse; and pesticides. Ligands and receptors are complementary members of a specific binding pair, each sbp member having an area on the surface or in a cavity which specifically binds to and is complementary with a particular spatial and polar organization of the other.

One embodiment of the invention is a method of preparing a fluorescent conjugate comprising combining a BDI dye of formula I with the sbp member being labeled. Another embodiment of the invention is a sbp member labeled with a new reactive BDI dye. Preferably the sbp member is a ligand, more preferably the ligand is a nucleotide, oligonucleotide, peptide, protein, lipid polysaccharide or carbohydrate.

To label a sbp member, the new BDI dyes of this reaction are combined with a sbp member of interest which sbp member is capable of reacting with the reactive group (G) on the BDI fluorophore. Generally, any sbp member containing one or more of the reactive sites listed in Table 1 can be labeled using the new dyes. Preferred reactive sites are amines, thiols or carboxylic acids. The sbp member may be monovalent (containing a single reactive site) or polyvalent (containing multiple reactive sites).

When the sbp member lacks a reactive site or reaction at the reactive site inhibits formation of a sbp pair interaction, an appropriate coupling moiety can often be introduced by synthesis or modifications familiar in the art. For example, the starting material for nucleic acid conjugates is an oligonucleotide (oligo) which has incorporated a reactive residue, typically an amine or thiol, to form a derivatized oligo. The reactive residue is attached through a carbon chain spacer of a variety of lengths at either a substituted nucleotide base or the 5' end of the oligo. The thiol- or amine-derivatized oligos are typically commercially available with a carbon chain spacer of about 2-12 carbons.

Typically, the reactive BDI dye is coupled directly to the sbp member. For example, if the sbp member is a ligand that has an amino substituent and the reactive dye has a carboxyl substituent, then the ligand and fluorophore may be directly conjugated to each other by procedures known in the art; for example, an active ester technique. Where the sbp member is a protein, it is less likely to require derivatization to add additional reactive sites. However, if desired, other groups can be introduced such as by thiolation with succinimidyl 2-pyridyldithiopropionate (SPDP).

A sbp member can be labeled with the BDI dyes by using procedures such as those illustrated in Examples 25-30. Generally, the derivatized or reactive sbp member is solubilized in an appropriate solvent. The conditions required for solubilizing sbp members are generally known in the art. The dye is solubilized in an appropriate solvent that is mutually miscible with the solvent that is used to solubilize the sbp member. For applications which require use of a water miscible solvent, appropriate solvents include, for example, methanol, ethanol, dimethylformamide (DMF), dimethylsulfoxide (DMSO), and acetone. For preparation of a conjugate where the sbp is water insoluble, appropriate solvents include, for example, DMF, DMSO, chloroform, toluene, and many other organic solvents.

The temperature at which the reaction for preparing the conjugates of this invention proceeds is not critical. The temperature should be one which is sufficient to initiate and maintain the reaction, without compromising the stability or activity of the sbp member or its conjugate. Generally, for convenience and economy, room temperature ($\sim 25°$ C.) is sufficient.

In preparing the conjugates of the present invention, the ratio of reactants is not narrowly critical. For each mole of reactive dye of formula I, one usually employs about one mole of the sbp member being labeled to obtain a reasonable yield. In some cases it is preferred to employ an excess of reactive dye for ease of reaction and sufficient labeling of the sbp member. For example, in preparing oligo conjugates, 50-100 fold excess of dye has been found to be appropriate. The combined reactants, dye and sbp member, are incubated for sufficient time to allow the conjugation to occur, which may range from about 10 minutes to 24 hours, more typically from about 30 minutes to about 12 hours.

Following attachment of the reactive dye to the sbp member, the conjugate is then purified using standard purification techniques, for example, using chromatography, crystallization, etc.

The dye-conjugated ligands are useful in a wide variety of areas as biochemical tools for the detection, identification, and measurement of biological compounds, particularly immunochemically reactive components such as those found in body fluids, cells, and cell components. For example, the labeled proteins can indicate the presence and amount of certain antigens or identify the site of certain immunochemical reactions, using known assay methods and imaging techniques for detection of the fluorescence signal. The labeled nucleotides and oligonucleotides can be used in research efforts directed at determining the presence or sequence of nucleic acids in genes, using known gene mapping techniques.

The following examples of the synthesis and characterization of the long wavelength reactive BDI dyes and the combination of such dyes with other natural and synthetic materials are intended to illustrate the generality of the invention and not to define or limit the scope of the invention.

EXAMPLE 1

4,4-Difluoro-3-(2-methoxycarbonylethyl)-5-(2-thienyl)-4-bora-3a,4a-diaza-s-indacene (Compound 1 ):

To a solution of 500 mg (2.82 mmol) of 2-formyl-5-(2-thienyl)pyrrole and 435 mg (2.84 mmol) of 2-(2-methoxycarbonylethyl) pyrrole in 50 mL of dichloromethane is added 265 μL (2.84 mmol) of phosphorus oxychloride. The reaction mixture is stirred at room temperature for 16 hours and then 2.0 mL (11.5 mmol) of N,N-diisopropylethylamine is added, followed by the addition of 1.5 mL (11.5 mmol) of boron trifluoride etherate. After the whole reaction mixture is stirred at room temperature for 2 hours, it is washed with two 50 mL portions of brine. The organic layer is separated, dried over anhydrous sodium sulfate and concentrated under reduced pressure to give a dark brown solid. The crude product is purified by chromatography on silica gel with chloroform as eluant to give 380 mg (52%) of Compound 1 as a dark purple solid.

The 2-formyl-5-(2-thienyl)pyrrole is prepared from 2-(2-thienyl)pyrrole by the Vilsmeier-Haack formylation, according to R. M. Silverstein et al., ORG. SYNTH. COLL. Vol. IV, p. 831. The 2-(2-thienyl)pyrrole needed for this synthesis is prepared in a similar manner as described in Kruse, et al., HETEROCYCLES 2.6, 3141 (1987).

The 2-(2-methoxycarbonylethyl)pyrrole is prepared as follows: A solution of pyrrole-2-carboxaldehyde (3.9 g, 41 mmol) and (carbomethoxymethylene)triphenylphosphorane (14 g, 42 mmol) in 160 mL of dry benzene is heated at reflux for 18 hours under a nitrogen atmosphere. After cooling, the reaction mixture is concentrated under vacuum and the resulting oil is purified by silica gel column chromatography, eluting with a mixture of ethyl acetate and hexane (1:9) to give 5.11 g of a mixture of cis- and trans-methyl 2-(2-pyrrolyl)acrylate.

It is then dissolved in 100 mL of methanol in a PARR shaker bottle and to this is added 500 mg 10% palladium on charcoal. The mixture is pressurized to 50 psi with hydrogen and shaken at room temperature for 2 hours. The reaction mixture is filtered through a diatomaceous earth pad and the filtrate is concentrated under vacuum to give 5.10 g (82%) of 2-(2-methoxycarbonylethyl)pyrrole as a pale yellow oil, $^1$H-NMR (CDCl$_3$) δ2.64(t,2H,CH$_2$), 2.92(t,2H,CH$_2$), 3.71(t,3H,CH$_3$), 5.93(d, 1H, ArH), 6.12(m, 1H,ArH), 6.68(d, 1H,ArH), 8.62 (bs, 1H,NH).

EXAMPLE 2

4,4-Difluoro-3-(2-methoxycarbonylethyl)-5-(2-furyl)-4-bora-3a,4a-diaza-s-indacene (Compound 5):

This is prepared in the same manner as described in Example 1 from 2-(2-methoxycarbonylethyl)pyrrole (240 mg, 1.56 mmol) and 2-formyl-5-(2-furyl)pyrrole (250 mg, 1.55 mmol). Compound 5 (295 mg, 55% yield) is obtained as a dark purple solid.

The 2-formyl-5-(2-furyl)pyrrole is prepared from 2-(2-furyl)pyrrole by the Vilsmeier-Haack formylation as described in ORG. SYNTH. COLL. Vol. IV, p. 831. The 2-(2-furyl)pyrrole needed for this synthesis is prepared in a similar manner as described in HETEROCYCLES 26, 3141 (1987).

EXAMPLE 3

4,4-Difluoro-3-(2-methoxycarbonylethyl)-5-(2-pyrrolyl)-4-bora-3a,4a-diaza-s-indacene (Compound 7):

To a solution of 150 mg (1.13 mmol) of 2,2'-bipyrrole and 205 mg (1.13 mmol) of 2-(2-methoxycarbonylethyl)-5-formylpyrrole in 10 mL of dichloromethane is added 110 μL ( 1.18 mmol) of phosphorus oxychloride. The reaction mixture is stirred at room temperature for 12 hours and then is added 800 μL (4.59 mmol) of N,N-diisopropylethylamine, followed by the addition of 560 μL (4.55 mmol) of boron trifluoride etherate, After the whole mixture is stirred at room temperature for 2 hours, it is washed with two 10 mL portions of brine. The organic layer is separated, dried over anhydrous sodium sulfate and concentrated under reduced pressure to give a dark red solid. The crude product is purified by chromatography on silica gel with a mixture of chloroform and hexane (1:1) as eluant to give 125 mg (32%) of Compound 7 as a dark purple solid.

The 2,2'-bipyrrole is prepared as described in Rappaport et al., J. AM. CHEM. SOC., 84, 2178 (1962). The 2-(2-methoxycarbonylethyl)-5-formylpyrrole is prepared from 2-(2-methoxycarbonylethyl)pyrrole by the Vilsmeier-Haack formylation according to ORG. SYNTH. COLL. Vol. IV, p 831.

EXAMPLE 4

4,4-Difluoro-1,3-dimethyl-2-(2-methoxycarbonylethyl)-5-(2-pyrrolyl)-4-bora-3a,4a-diaza-s-indacene (Compound 10):

This is prepared in the same method as described in Example 3 from 2,2'-bipyrrole (500 mg, 3.78 mmol) and 2.4-dimethyl-5-formyl-3-(2-methoxycarbonylethyl)pyrrole (795 mg, 3.80 mmol). Compound 10 (760 mg, 54%) is obtained as a dark purple solid.

The 2,4-dimethyl-5-formyl-3-(2-methoxycarbonylethyl)pyrrole is prepared from 2,4-dimethyl-3-(2-methoxycarbonylethyl)pyrrole by the Vilsmeier-Haack formylation as described in ORG. SYNTH. COLL. Vol. IV, p 831. The 2,4-dimethyl-3-(2- methoxycarbonylethyl)pyrrole is prepared as described in Bullock, et al., J. CHEM. SOC. 1420 (1958).

EXAMPLE 5

4,4-Difluoro-1,3-dimethyl-8-(2-methoxycarbonylethyl)-5-(2-thienyl)-4-bora-3a,4a-diaza-s-indacene (Compound 12):

To a solution of 500 mg (2.39 mmol) of methyl 4-[2-(3,5-dimethyl)pyrrolyl]-4-oxobutanoate and 355 mg (2.38 mmol) of 2-(2-thienyl)pyrrole in 30 mL of dichloromethane is added 230 μL (2.47 mmol) of phosphorous oxychloride. The reaction mixture is heated under reflux in a nitrogen atmosphere for 2 days. It is cooled to room temperature and then is added 1.7 mL (9.76 mmol) of N,N-diisopropylethylamine, followed by addition of 1.2 mL (9.76 mmol) of boron trifluoride etherate. After the whole reaction mixture is stirred at room temperature for 4 hours, it is washed with two 30 mL portions of brine. The organic layer is separated, dried over anhydrous sodium sulfate and concentrated under reduced pressure. The crude product is purified by chromatography on silica gel with a mixture of chloroform and hexane (1:1) to give 340 mg (34%) of Compound 12 as a dark red solid.

The methyl 4-[2-(3,5-dimethyl)pyrrolyl]-4-oxobutanoate is prepared as described in Treibs, et al., LIEBIGS. ANN. CHEM., 702, 112 (1967).

EXAMPLE 6

4,4-Difluoro-3-[4-(methoxycarbonylmethoxy)phenyl]-5-(2-thienyl)-4-bora-3a,4a-diaza-s-indacene (Compound 14):

This is prepared in the same method as described in Example 1 from 2-[4-(methoxycarbonylmethoxy)-phenyl]pyrrole (100 mg, 0.43 mmol) and 2-formyl-5-(2-thienyl)pyrrole (75 mg, 0.42 mmol). Compound 14 (68 mg, 37%) is obtained as a dark purple solid.

The 2-[4-(methoxycarbonylmethoxy)phenyl]pyrrole needed for this synthesis is prepared as follows: To a suspension of 1.0 g (11.9 mmol) of ethanethiol, sodium salt in 10 mL of dry DMF is added 2.0 g (11.5 mmol) of 2-(4-methoxyphenyl)pyrrole [prepared in a similar method as described in HETEROCYCLES 26, 3141 (1987)] while the reaction mixture is stirred in an ice bath under nitrogen atmosphere. It is then stirred at 110° C. for 4 hours. After the reaction mixture is cooled to room temperature, 1.82 g (11.9 mmol) of methyl bromoacetate is added. After stirring at room temperature for 2 hours, it is poured into ice-water (100 mL). It is extracted with chloroform (3×70 mL). It is dried over anhydrous sodium sulfate and concentrated under reduced pressure to give a brown solid. The crude product is purified by chromatography on silica gel with chloroform as eluant to give 1.92 g (68%) of the 2-[4-(methoxycarbonylmethoxy)phenyl]pyrrole as an off-white solid; m.p. 136°–137°, $R_f$=0.30 in chloroform, $^1$H-NMR (CDCl$_3$) δ3.82(s,3H,CH$_3$), 4.65(s,2H,CH$_2$), 6.26–6.29(m,1H,ArH), 6.40–6.44(m, 1H, ArH), 6.81–6.84(m,1H,ArH), 6.91(d,2H,ArH), 7.40(d,2H,ArH).

The Compounds 17, 22, 25, and 39 are prepared by the reaction of 2-formyl-5-(2-furyl)pyrrole; 2-formyl-5-[(E)-2-phenylethen-1-yl]pyrrole, 2-formyl-5-[(E,E)-4-phenyl-1,3-butadien-1-yl]pyrrole, 2-formyl-5-[(E)-propen-1-yl]pyrrole, respectively, with 2-[4-(methoxycarbonylmethoxy)phenyl]pyrrole as described in Example 6. Compound 19 is prepared by the reaction of 2,2'-bipyrrole with 2-formyl-5-[4-(methoxycarbonylmethoxy)phenyl]pyrrole, which is obtained by the Vilsmeier-Haack formylation of 2-[4-(methoxycarbonylmethoxy)-phenyl]pyrrole, as described in Example 6.

EXAMPLE 7

4,4-Difluoro-3-[(E)-2-[4-(methoxycarbonylmethoxy)-phenyl]ethen-1-yl]-5-[(E)-2-phenylethen-1-yl]-4-bora-3a,4a-diaza-s-indacene (Compound 23):

This is prepared in the same manner as described in Example 1 from 2-formyl-5-[(E)-phenylethen-1-yl]pyrrole (75 mg, 0.38 mmol) and 2-[(E)-2-[(4-methoxycarbonylmethoxy)phenyl]ethen-1-yl]pyrrole (100 mg, 0.39 mmol). The Compound 23 (59 mg, 32%)is obtained as a dark blue solid.

The 2-[(E)-2-[4-(methoxycarbonylmethoxy)phenyl]ethen-1-yl]pyrrole needed for this synthesis is prepared in the similar way as described in Example 6 by the reaction of 2-[(E)-2-(4-methoxyphenyl)ethen-1-yl]pyrrole with ethanethiol, sodium salt, and methyl bromoacetate in DMF.

EXAMPLE 8

4,4-Difluoro-3-(2-methoxycarbonylethyl)-5-[(E)-2-phenylethyl-1-yl]-4-bora-3a,4a-diaza-s-indacene (Compound 45):

To a solution of 3.0 g (15.2 mmol) of 2-formyl-5-[(E)-2-phenylethyl-1-yl]pyrrole and 2.33 g (15.2 mmol) of 2-(2-methoxycarbonylethyl)pyrrole in 70 mL of dichloromethane is added 1.45 mL (15.6 mmol) of phosphorus oxychloride. After the reaction mixture is stirred at room temperature for 18 hours, 10 mL (57.4 mmol) of N,N-diisopropylethylamine, is added followed by the addition of 7 mL (56.9 mmol) of boron trifluoride etherate. It is stirred at room temperature for 3 hours and worked up in the same manner as described in Example 1 to give 3.57 g (62%) of Compound 45 as a dark red-purple solid.

Compounds 27, 38, and 44 are prepared by the reaction of 2-formyl-5-[(E,E)-4-phenyl-1,3-butadien-1-yl]pyrrole, 2-formyl-5-[(E)-propen-1-yl]pyrrole and 2-formyl-5-[(E)-2-(1-naphthyl)ethen-1-yl)pyrrole, respectively, with 2-(2-methoxycarbonylethyl)pyrrole as described in Example 8.

Compounds 30, 36, 37 and 41 are prepared by the reaction of 2-[(E)-2-carbomethoxyethen-1-yl]pyrrole, 2-[(E)-2-(5-carboethoxy-4-methyl-2-oxazolyl)ethen-1-yl]pyrrole, 2-[(E)-2-(5-carbomethoxy-4-methyl-2-oxazolyl)ethen- 1-yl]-pyrrole and 2-[(E)-2-(4-carbomethoxyphenyl)ethen-1-yl]pyrrole, respectively, with 3,5-dimethylpyrrole-2-carboxaldehyde as described in Example 8.

Compound 33 is prepared from 2-[(E)-2-carbomethoxyethen-1-yl]pyrrole and 3,5-diphenylpyrrole-2-carboxaldehyde in the similar way as described in Example 8.

Most of the key intermediates needed for the synthesis of Compounds 22, 23, 25, 27, 30, 33, 36, 37, 38, 39, 41, 44 and 45 are prepared from the appropriately selected starting materials. As a typical example, 2-[(E)-2-(4-carbomethoxyphenyl)ethen-1-yl]pyrrole needed for the synthesis of Compound 41 is 3 prepared as follows: A mixture of 1.0 g (10.5 mmol) of pyrrole-2-carboxaldehyde, 2.5 g (10.9 mmol) of methyl 4-bromoethylbenzoate, 2.2 g (10.9 mmol) of tributylphosphine and 700 mg of zinc is heated at 100° C. in a stream of nitrogen for 15 hours. After cooling to room temperature, the whole reaction mixture is treated with 50 mL of chloroform. It is washed several times (3×50 mL) with water. The organic layer is dried with anhydrous sodium sulfate and concentrated under reduced pressure. The crude product is purified by chromatography on silica gel with 30% chloroform in hexane as eluant to give 427 mg (18%) of the product as a white solid; m.p. 120°–121° C., $^1$H-NMR (CDCl$_3$) δ3.90(s,3H,CH$_3$), 6.26–6.29(m,1H,ArH), 6.42–6.45(m, 1H,ArH), 6.69(d, 1H,CH=), 6.84–6.88(m, 1H,ArH), 7.08(d,1H,CH=), 7.45(d,2H,2×ArH), 7.99(d,2H,2×ArH), 8.55(bs,1H,NH).

EXAMPLE 9

4,4-Difluoro-3-(2-carboxyethyl)-5-(2-thienyl)-4-bora-3a,4a-diaza-s-indacene (Compound 2):

To a solution of 3.0 g (8.33 mmol) of Compound 1 in 200 mL of tetrahydrofuran are added 100 mL of water and 12 mL of 85% phosphoric acid and the whole mixture is heated under reflux for 4 days. After cooling to room temperature, the reaction mixture is concentrated under reduced pressure to remove most of the tetrahydrofuran. The resulting aqueous residue is extracted with chloroform. The chloroform layer is dried over anhydrous sodium sulfate and concentrated under reduced pressure to give a purple-red oil. The crude product is subjected to silica gel column chromatography. It is first eluted with chloroform to give 0.65 g of an unreacted starting material 1. It is then eluted with 1% methanol in chloroform to afford 1.75 g (61%) of Compound 2 as a dark purple solid.

Compounds 6, 8, 15, 18, 20, 2.4, 26, 28 31, 34, 40, and 46 which contain a carboxylic acid as a reactive group, are prepared by hydrolysis of the corresponding esters 5, 7, 14, 17, 19, 23, 25, 27, 30, 33, 39 and 45 as described in the preparation of Compound 2 in Example 9.

EXAMPLE 10

Succinimidyl ester (Compound 3):

To a solution of 650 mg (1.88 mmol) of Compound 2 in 70 mL of tetrahydrofuran is added 230 mg (1.99 mmol) of N-hydroxysuccinimide followed by addition of 410 mg (1.99 mmol) of N,N'-dicyclohexylcarbodiimide. The mixture is stirred at room temperature for 24 hours. The resulting precipitate is removed by filtration and the filtrate is evaporated to dryness under reduced pressure to give a crude product. It is purified by chromatography on silica gel with chloroform as eluant to give 715 mg (86%) of Compound 3 as a dark purple solid.

Compounds 9, 16, 21, 29, 32, 35 and 47, which contain a succinimidyl ester as a reactive group, are prepared from the corresponding carboxylic acids 8, 15, 20, 28, 31, 34 and 46 by the similar method as described in the preparation of Compound 3 in Example 10.

EXAMPLE 11

Hydrazide (Compound 4):

To a solution of 10 µL of anhydrous hydrazine in 1 mL of chloroform is added 25 mg of Compound 3 and the mixture is stirred at room temperature for 30 minutes. The reaction mixture is diluted with 15 mL of chloroform, washed with water, dried over anhydrous sodium sulfate and concentrated under reduced pressure to give a crude product. It is purified by silica gel column chromatography with 2% methanol in chloroform as eluant to give 21 mg (98%) of Compound 4.

EXAMPLE 12

Amine (Compound 48):

To a solution of 150 µL (2.24 mmol) of ethylenediamine in 2 mL of chloroform is added a solution of 100 mg (0.22 mmol) of Compound 47 in 3 mL of chloroform dropwise over a period of 10 minutes and the mixture is stirred at room temperature for 1 hour. It is then diluted with 15 mL of chloroform, washed with water (3×20 mL), dried over anhydrous sodium sulfate and concentrated under reduced pressure to give a crude product. It is purified by chromatography on silica gel with 10% methanol in chloroform as eluant to give 75 mg (85%) of the amine 48. Compound 61 is prepared from Compound 3 by the same method as described in Example 12.

EXAMPLE 13

Iodoacetamide (Compound 49):

To a suspension of 20 mg (0.05 mmol) of Compound 48 in 3 mL of chloroform is added 10 µL of triethylamine, followed by addition of 12 mg (0.05 mmol) of iodoacetic anhydride and the mixture is stirred at room temperature for 2 hours. After evaporation under reduced pressure, it is purified by silica gel column chromatography with 2% methanol in chloroform as eluant to give 19 mg (67%) of the iodoacetamide 49. Compound 62 is prepared from Compound 61 by the same method as described in Example 13.

EXAMPLE 14

Maleimide (Compound 50):

To a suspension of 20 mg (0.05 mmol) of Compound 48 in 3 mL of chloroform is added 10 µL of chloroform is added 10 µL of triethylamine, followed by addition of 13 mg (0.05) of succinimidyl maleimidylacetate and the mixture is stirred at room temperature for 2 hours. It is concentrated and purified by column chromatography on silica gel with 2% methanol in chloroform as eluant to give 18 mg (67%) of the maleimide 50.

EXAMPLE 15

Aldehyde (Compound 51):

To a suspension of 20 mg (0.05 mmol) of Compound 48 in 3 mL of chloroform is added 10 µL of triethylamine, followed by addition of 12 mg (0.05 mmol) of succinimidyl p-formylbenzoate and the mixture is stirred at room temperature for 2 hours. It is concentrated and purified by column chromatography on silica gel with 2% methanol in chloroform as eluant to give 22 mg (83%) of the aldehyde 51.

EXAMPLE 16

Azide (Compound 52):

To a suspension of 20 mg (0.05 mmol) of Compound 48 in 3 mL of chloroform is added 10 µL of triethylamine, followed by addition of 13 mg (0.05 mmol) of succinimidyl p-azidobenzoate. After stirring at room temperature for 2 hours, it is concentrated under reduced pressure and purified by column chromatography on silica gel eluting with 1% methanol in chloroform to give 17 mg (63%) of the azide 52.

EXAMPLE 17

Acrylamide (Compound 53):

To a suspension of 20 mg (0.05 mmol) of Compound 48 in 3 mL of chloroform is added 10 µL of triethylamine, followed by addition of 9 mg (0.05 mmol) of succinimidyl acrylate and the mixture is stirred at room temperature for 2 hours. After concentration under reduced pressure, it is purified by silica gel column chromatography with 1% methanol in chloroform as eluant to give 18 mg (79%) of the acrylamide 53.

EXAMPLE 18

Alcohol (Compound 42):

To a solution of 125 mg (1.01 mmol) of 3,5-dimethylpyrrole-2-carboxaldehyde and 200 mg (1.00 mmol) of 2-[(E)-2-(4-hydroxymethylphenyl)ethen-1-yl]pyrrole in 15 mL of dichloromethane is added 100 µL (1.07 mmol) of phosphorus oxychloride. The reaction mixture is stirred at room temperature for 24 hours and then is added 700 µL (4.02 mmol) of N,N-diisopropylethylamine, followed by addition of 490 µL (3.98 mmol) of boron trifluoride etherate. After the whole mixture is stirred at room temperature for 2 hours, it is washed with two 15 mL portions of water. The organic layer is separated, dried over anhydrous sodium sulfate and concentrated under reduced pressure to give a dark red oil. The crude product is subjected to silica gel column chromatography. It is first eluted with 1:1 hexane/- chloroform to give 32 mg of the chloride, Compound 43, as a dark red solid. It is then eluted with chloroform to afford 75 mg (21%) of the alcohol, compound 42, as a dark red solid.

The compound 2-[(E)-2-(4-hydroxymethylphenyl)ethen-1-yl]pyrrole needed for this synthesis is prepared as follows: To a solution of 1.0 g (4.4 mmol) of 2-[(E)-2-(4-carbomethoxyphenyl)ethen-1-yl]pyrrole in 20 mL of dry tetrahydrofuran is added 167 mg (4.4 mmol) of lithium aluminum hydride portionwise while the reaction mixture is stirred at 0° C. under nitrogen atmosphere. After addition is complete, it is stirred at room temperature for 15 hours. It is then cooled with an ice-water bath and the excess lithium aluminum hydride is destroyed by the slow addition of 2 mL water. The reaction mixture is concentrated under reduced pressure to remove most of the tetrahydrofuran. The resulting residue is extracted with chloroform (3×50 mL), dried over anhydrous sodium sulfate and concentrated to give 0.68 g (78%) of 2-[(E)-2-(4-hydroxymethylphenyl)ethen-1-yl]pyrrole as an off-white solid, m.p. 186°–189° C.; $^1$H-NMR(CDCl$_3$) δ4.69 (s,2H,CH$_2$), 6.24–6.27(m,1H,ArH), 6.35–6.37(m,1H,ArH), 6.66(d,1H, =CH), 6.81–6.84(m,1H,ArH), 6.98(d,1H, =CH), 7.33(d,2H,ArH), 7.44(d,2H,ArH), 8.36(bs,1H,NH).

EXAMPLE 19

Halide (Compound 43):

To a solution of 20 mg (0.06 mmol) of Compound 42 in 5 mL of dichloromethane is added one drop of triethylamine, followed by the addition of 5 mg (0.03 mmol) of cyanuric chloride. The mixture is stirred at room temperature for 1 hour. It is then subjected to silica gel column chromatography with 1:1 hexane/chloroform as eluant to give 15 mg (71%) of the halide 43.

EXAMPLE 20

Isothiocyanate (Compound 54):

To a suspension of 30 mg (0.07 mmol) of Compound 48 in 5 mL of chloroform is added 20 μL of triethylamine, followed by the addition of 10 μL (0.13 mmol) of thiophosgene and the mixture is stirred at room temperature for 1 hour. It is concentrated under reduced pressure and the resulting residue is purified by column chromatography on silica gel with chloroform as eluant to give 22 mg (66%) of the isothiocyanate 54.

EXAMPLE 21

Anhydride (Compound 55):

To a suspension of 30 mg (0.09 mmol) of Compound 2 in 5 mL of chloroform is added 15 μL of triethylamine, followed by addition of 10 μL of ethyl chloroformate and the mixture is stirred at room temperature for 1 hour. Without isolation of the anhydride, Compound 55, it is characterized as its n-butyl amide, Compound 58, by addition of 15 μL of n-butylamine to the reaction mixture. The crude residue isolated by evaporation of the reaction mixture is purified by column chromatography on silica gel with chloroform as eluant to yield 29 mg (85%) of the Compound 58.

EXAMPLE 22

Acyl azide (Compound 56):

To a suspension of 30 mg (0.09 mmol) of Compound 2 in 5 mL of chloroform is added 15 μL of triethylamine, followed by the addition of 20 μL (0.09 mmol) of diphenylphosphoryl azide and the reaction mixture is stirred at room temperature for 3 hours. It is concentrated under reduced pressure and purified by column chromatography on silica gel, eluting with chloroform to give 17 mg (53%) of the acyl azide 56.

EXAMPLE 23

Carbonyl fluoride (Compound 57):

To a solution of 10 mg (0.03 mmol) of Compound 2 and 3 μL of pyridine in 5 mL of dichloromethane is added 2 μL of cyanuric fluoride and the mixture is stirred at room temperature for 30 minutes. Without isolation of the carbonyl fluoride, Compound 57, it is characterized as its n-butyl amide, Compound 58 (10 mg, 90% yield) as described in Example 21.

EXAMPLE 24

Sulfonyl Chloride (Compound 60):

To an ice-cooled solution of 30 mg (0.08 mmol) of 4,4-difluoro-3,5-bis[(E)-2-phenylethen-1-yl]-4-bora-3a,4a-diaza-s-indacene (which is prepared from 2-[(E)-2-phenylethen-1-yl]pyrrole and 2-formyl-5-[(E)-2-phenylethen-1-yl]pyrrole as described in Example 1) in 3 mL of dichloromethane is added 12 μL (0.18 mmol) of chlorosulfonic acid and the mixture is stirred at 0° C. for ½ hours under nitrogen atmosphere. The resulting precipitate is collected by filtration, dissolved in 1 mL of water and the solution is treated with 20 mg of sodium bicarbonate. The crude product is purified by chromatography over lipophilic Sephadex using water for elution and the desired fractions are combined and lyophilized to give 12 mg of Compound 59. To 300 μL of thionyl chloride is added 30 μL of dry dimethylformamide and the mixture is stirred at room temperature for 10 minutes. To the above solution is added 10 mg of Compound 59 and the mixture is stirred at room temperature for 2 hours. The resulting reaction mixture is treated with 10 mL of chloroform. It is poured into 10 mL of ice water and shaken vigorously for a few minutes. The chloroform layer is separated, dried over anhydrous sodium sulfate and concentrated under reduced pressure to give 7 mg of the sulfonyl chloride 60 as a dark blue solid.

EXAMPLE 25

Sphingosine Conjugate (Ceramide):

To a solution of 5 mg of D-sphingosine (Sigma Chemical Co., St. Louis, Miss.) in 1 mL of chloroform are added 5 μL of triethylamine and 9 mg of Compound 47 and the mixture is stirred at room temperature for 12 hours. The reaction mixture is subjected to chromatography on silica gel with 1% methanol in chloroform. From the desired combined fractions 7 mg of a fluorescent ceramide is obtained: m.p. 77°–79° C., $R_f$=0.51 (10% methanol in chloroform), absorption maximum: 564.5 nm in methanol, emission maximum: 571 nm in methanol.

EXAMPLE 26

Nucleotide Conjugate:

To a solution of 2 mg of 5-(3-aminoallyl)-2'-deoxyuridine-5'-triphosphate, ammonium salt (Sigma Chemical Co., St. Louis, Miss.) in 200 μL of water is added a solution of 2 mg of Compound 3 in 200 μL of acetonitrile, followed by addition of 5 μL of triethylamine. After the mixture is stirred at room temperature for 3 hours, it is purified by chromatography over lipophilic SEPHADEX resin using water for elution. The desired fractions are combined and lyophilized to give 2 mg of the fluorescent nucleotide: $R_f$=0.47 (10:5:9:9/dioxane:2-propanol:water:ammonium hydroxide), absorption maximum: 558.6 nm in pH 7 phosphate buffer; emission maximum: 570 nm in pH 7 phosphate buffer.

EXAMPLE 27

Oligonucleotide Conjugate:

The 5'-amine-derivatized oligonucleotide of sequence X TGTAAAACGA CGGCCAGT (SEQ ID NO:1), where X, the last phosphoramidite (5' end) is the commercially available C6 aminolink-TFA obtained from Glen Research Inc., Sterling, Va., is prepared by automated solid phase synthesis on a ABI 380A using the standard 1 µM synthesis cycle. After the standard cleavage from the solid phase column and deblocking in concentrated aqueous ammonia (5 hours at 55° C.), the oligonucleotide is concentrated on a vortex evaporator to dryness in a 15 mL plastic centrifuge tube. The oligonucleotide is desalted with a Bio-Rad 10DG desalting column, Bio-Rad Labs, Richmond, Calif., using the standard procedure. The oligonucleotide is aliquoted into convenient 10 ODU portions in 2 mL microcentrifuge tubes and evaporated on a speed-vac. The 5'-amine-derivatized oligonucleotide, 10 ODU (350 µg, 0.055 µM) dissolved in 250 µL of 0.5M $NaHCO_3/Na_2CO_3$ pH 9 aqueous buffer in the microcentrifuge tube. The compound 16, 2 mg (3.8 µM), is dissolved in 200 µL of DMF and added to the oligonucleotide solution. This is shaken by hand and allowed to sit for 16 hours. 1 mL of 0.1M TEAA is added and the solution is passed through a Bio-Rad 10 DG desalting column substituting 0.1M TEAA for deionized water in the standard procedure. The second 2 mL fraction is collected and evaporated in a 15 mL centrifuge tube on a vortex evaporator. The labeled oligonucleotide is then HPLC purified on a 220 mm×10 mm 300 Å C8 reverse phase column, Rainin Instrument Co., Woburn, Mass., using the following gradient: Solvent A-0.1M TEAA, Solvent B-acetonitrile. Ramp solvent B from 15% to 95% over 40 minutes then hold at 95% for 5 minutes. Detection is with a Waters 490 dual wavelength UV-Vis detector monitoring 254 nm and 590 nm. The appropriate peak is collected and evaporated to give 2.3 ODU (80 µg, 0.013 µM) 24% yield.

Example 28

Protein Conjugates:

The succinimidyl esters, Compounds 3 and 16, are dissolved to give a concentration of 10 mg dye/mL DMF. Bovine serum albumin (BSA) or other proteins are dissolved to a concentration of approximately 10 mg protein/mL in 0.1M sodium bicarbonate. Amicon GH-25 desalting media in phosphate buffered saline (PBS) and 1.5M hydroxylamine pH 8 are freshly prepared. The appropriate amount of each dye in DMF corresponding to a molar ratio of 10 (dye/protein) is slowly added to the separate protein solutions with stirring. Each reaction is incubated at room temperature for one hour and is then terminated by the addition of hydroxylamine to a final concentration of 0.15M. Following incubation for an additional thirty minutes the protein conjugates are separated from free unreacted dye in the two solutions by gel filtration on a GH-25 column equilibrated in PBS. The initial, protein-containing fractions from each solution are pooled and the degree of substitution is determined from the extinction coefficient for each dye at its absorption maximum (559 nm for Compound 3 and 590 nm for Compound 16). An approximate degree of substitution of 3 (dye/BSA) is determined for both cases. The fluorescence of each final protein conjugate is approximately 10% of the free dye.

R-phycoerythrin, avidin, epidermal growth factor, immunoglobulins, concanavalin A, wheat germ agglutinin, protein A are conjugated with succinimidyl esters using essentially the same procedure.

EXAMPLE 29

Peptide Conjugate:

To a suspension of 5 mg of Xaa Leu Phe Xaa Tyr Lys (SEQ ID NO:2) (Bachem. Inc., Torrance, Calif., where Xaa in the first position is N-formyl norleucine and Xaa in the fourth position is norleucine, in 500 µL of dimethylformamide is added 3 µL of triethylamine followed by the addition of 3 mg of Compound 3 and the whole reaction mixture is stirred at room temperature for 30 minutes. The reaction mixture is purified by chromatography over lipophilic SEPHADEX yesin using water for elution. The desired fractions are combined and lyophilized to give 4 mg of the fluorescent hexapeptide.

Example 30

Carbohydrate Conjugate:

To a solution of 5 mg of 6-amino-6-deoxy-D-glucose hydrochloride (U.S. Biochemical Corp., Cleveland, Ohio in 0.5 mL of water and 1 mL of tetrahydrofuran is added 5 µL of triethylamine followed by the addition of 10 mg of Compound 3. After the mixture is stirred at room temperature for 1 hour, it is purified by chromatography over silica gel using 10% methanol in chloroform. From the desired combined fractions 12 mg of a fluorescent carbohydrate is obtained: m.p. 99°–102° C., $R_f$=0.53 (25% methanol in chloroform), absorption maximum: 559.0 nm in methanol, emission maximum: 570 nm in methanol.

EXAMPLE 31

Determination Of The Chemical Reactivity Of The Dyes:

The chemically reactive dyes that are the subject of this invention are subjected to incubation in aqueous, methanolic, or chloroform solution with model compounds and their reactivity is demonstrated by thin layer chromatography in a solvent that separates the reactive dye from its products with visual detection of the fluorescence emission. It is demonstrated that n-butylamine reacts to form a new product with 3, 9, 16, 21, 32, 35, 47, 54, 55, 56, and 57, that 2-mercaptoethanol reacts with 43, 49, 50, and 62 that acetic anhydride reacts with 4, 42, 48, and 61, that acetone reacts with 4, that hydrazine reacts with 51, and that brefeldin A reacts with 2 in the presence of N,N'-dicyclohexylcarbodiimide to give an ester. Furthermore, it is demonstrated that the esters such as 1 can react with hydrazine to give hydrazides such as 4.

EXAMPLE 32

Spectral Characterization Of The Dyes:

$^1H$ NMR spectra are measured using a General Electric QE-400 MHz spectrometer for solutions in $CDCl_3$ (unless otherwise stated), with tetramethylsilane (TMS) as an internal standard. Chemical shifts are given in ppm from TMS and splitting patterns are designated as: s, singlet; d, doublet; t, triplet; m, multiplet. Results of spectral data for representative new dyes are given in Table 4.

Absorption spectra are obtained using an IBM 9429 UV/visible spectrophotometer by dissolving the dye at a concentration of approximately $5\times 10^{-6}M$ in an appropriate solvent including but not limited to methanol, chloroform, acetonitrile, acetone or hexane. Extinction coefficients ($\epsilon$) of the dyes at their absorption maxima are determined by standard Beer's law calculations. Results of the spectral determination for representative new dyes are tabulated in Table. 3 and Table 5.

Fluorescence of new long wavelength reactive dipyrromethaneboron difluoride dyes is determined using a Perkin-Elmer Model 650-40 fluorescence spectrophotometer equipped with a Perkin-Elmer/Hitachi 057 X-Y recorder by dissolving the dye at a concentration of above $1\times 10^{-10}M$ (optimum concentration ranges, $10^{-6} \sim 10^{-7}M$) in an appropriate solvent including but not limited to methanol, water, ethanol, acetonitrile, acetone, chloroform, toluene or hexane. Results of the spectral determination for representative new dyes are summarized in Table 3 and Table 5. Fluorescence can also be observed for the dyes in solution or on thin layer chromatography (TLC) plates, by visual inspection with illumination by a suitable source that gives off light below 650 nm.

EXAMPLE 33

Photobleaching Studies:

Photostability measurements of new long wavelength reactive BDI dyes are conducted in acetonitrile solution with continuous illumination by a 250 watt xenon arc lamp with 20 nm slit width at the corresponding excitation maxima. After thirty minutes of continuous illumination while stirring at room temperature in a cuvette of a fluorometer, emission intensity data is collected with 2.5 nm slit width at the emission maxima of individual samples. The results are listed in Table 5, together with that of the alkyl-substituted BDI dye, Compound R, for comparison (also shown in FIG. 4). Concentrations of individual samples are prepared to have the same optical density for all of the dyes at the respective excitation wavelength.

It will be obvious to one skilled in the art that synthesis of many other long wavelength reactive 4,4-difluoro-4-bora-3a,4a-diaza-s-indacene dyes that contain other bathochromic moieties can be accomplished using other appropriate pyrrole precursors that contain substituents compatible with the chemistry in FIG. 1 and such long wavelength reactive 4,4-difluoro-4-bora-3a,4a-diaza-s-indacene dyes from other appropriately substituted pyrrole precursors will fall within the description of the invention as described in the following claims.

---

What is claimed is:

1. A dye-conjugate comprising a specific binding pair member (sbp) and one or more dye molecules of the formula:

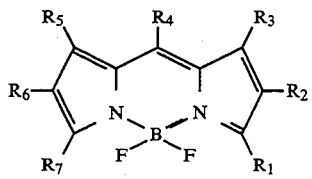

wherein at least one of the substituents $R_1$–$R_7$ covalently binds each dye molecule to the specific binding pair member; wherein, further, at least one of the substituents $R_1$–$R_7$ contains a linking bathochromic moiety or separate bathochromic moiety that is an ethenyl, dienyl, trienyl, or heteroaryl, and which is optionally substituted or unsubstituted; and the remaining substituents $R_1$–$R_7$, which may be the same or different, are hydrogen; halogen; sulfo or a sodium salt thereof; cycloalkyl; alkyl or arylalkyl, the alkyl portion of which contains 1–5 carbon atoms; or aryl, which may be further substituted, one or more times, by alkyl or alkoxy, the alkyl portions of which have less than 5 carbon atoms; or combinations thereof.

2. A dye-conjugate according to claim 1, wherein sbp is a nucleotide.

3. A dye-conjugate according to claim 1, wherein sbp is an oligonucleotide.

4. A dye-conjugate according to claim 1, wherein sbp is a peptide or a protein.

5. A dye-conjugate according to claim 4, wherein the protein is an antibody.

6. A dye-conjugate according to claim 4, wherein the protein is avidin or streptavidin.

7. A dye-conjugate according to claim 1, wherein sbp is a drug.

8. A dye-conjugate according to claim 1, wherein one of $R_1$–$R_7$ contains a heteroaryl group that is a pyrrolyl, thienyl, furanyl, oxazolyl, isoxazolyl, oxadiazolyl, imidazolyl, benzoxazolyl, benzothiazolyl, benzimidazolyl, benzofuranyl, or indolyl, that optionally contains substituents that are independently aryl, arylalkyl, alkyl, or alkoxy groups, the alkyl portions of which have fewer than 5 carbons, or a second heteroaryl that optionally contains substituents that are independently aryl, arylalkyl, alkyl, or alkoxy groups, the alkyl portions of which have fewer than 5 carbons, or combinations thereof.

9. A dye-conjugate as claimed in claim 8, wherein the heteroaryl group is a 2-pyrrolyl or 2-thienyl.

10. A dye-conjugate according to claim 1, wherein one of $R_1$–$R_7$ contains an alkenyl group that is ethenyl, butadienyl or hexatrienyl, that optionally contains substituents that are independently hydrogen, halogen, alkyl (containing 1–5 carbons), cyano, carboxylate ester, carboxamide, aryl or heteroaryl, that optionally contains substituents that are independently aryl, arylalkyl, alkyl, or alkoxy groups, the alkyl portions of which have fewer than 5 carbons, or combinations thereof.

11. A dye-conjugate as claimed in claim 1 wherein one or more dye molecules are linked to the sbp through a bond that is an amide, an ester, an ether, a thioether, a urea, a thiourea, an amidine, or an alkyl amine.

12. A dye-conjugate as claimed in claim 1 wherein the dye molecule is separated from the sbp by a linker containing 1–5 carbons.

13. A dye-conjugate as claimed in claim 1, wherein $R_2$ or $R_6$, or $R_2$ and $R_6$ are sulfo or a sodium salt thereof.

14. A dye-conjugate comprising a specific binding pair member (sbp) and one or more dye molecules of the formula:

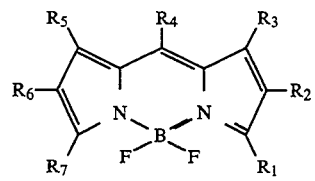

wherein at least one of the substituents $R_1$–$R_3$ covalently binds said dye molecule to the specific binding pair member that is a nucleotide or an oligonucleotide;

wherein, further, at least one of the substituents $R_1$–$R_3$ contains a linking bathochromic moiety or separate bathochromic moiety that is an ethenyl, dienyl, trienyl, or heteroaryl, and which is optionally substituted or unsubstituted; and the remaining substituents $R_1$–$R_7$, which may be the same or different, are hydrogen; halogen; sulfo or a sodium salt thereof; alkyl or arylalkyl, the alkyl portions of which contain 1–5 carbon atoms; or aryl, which may be further substituted, one or more times, by alkyl or alkoxy, the alkyl portions of which have less than 5 carbon atoms; or combinations thereof.

15. A dye-conjugate according to claim 14, wherein one of $R_1$–$R_3$ contains a heteroaryl group that is a pyrrolyl, thienyl, furanyl, oxazolyl, isoxazolyl, oxadiazolyl, imidazolyl, benzoxazolyl, benzothiazolyl, benzimidazolyl, benzofuranyl, or indolyl, that optionally contains substituents that are independently aryl, arylalkyl, alkyl, or alkoxy groups, the alkyl portions of which have fewer than 5 carbons, or a second heteroaryl that optionally contains substituents that are independently aryl, arylalkyl, alkyl, or alkoxy groups, the alkyl portions of which have fewer than 5 carbons, or combinations thereof.

16. A dye-conjugate according to claim 14, wherein one of $R_1$–$R_3$ contains an alkenyl group that is ethenyl, butadienyl or hexatrienyl, that optionally contains substituents that are independently hydrogen, halogen, alkyl (containing 1–5 carbons), cyano, carboxylate ester, carboxamide, aryl or heteroaryl, that optionally contains substituents that are independently aryl, arylalkyl, alkyl, or alkoxy groups, the alkyl portions of which have fewer than 5 carbons, or combinations thereof.

17. A dye-conjugate comprising a specific binding pair member (sbp) and one or more dye molecules of the formula:

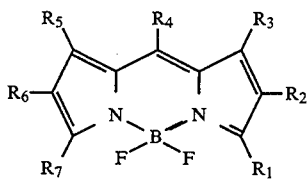

wherein at least one of the substituents $R_1$–$R_3$ covalently binds said dye molecule to the specific binding pair member that is a protein;

wherein, further, at least one of the substituents $R_1$–$R_3$ contains a linking bathochromic moiety or separate bathochromic moiety that is an ethenyl, dienyl, trienyl, or heteroaryl, and which is optionally substituted or unsubstituted; and the remaining substituents $R_1$ –$R_7$, which may be the same or different, are hydrogen; halogen; sulfo or a sodium salt thereof; alkyl or arylalkyl, the alkyl portions of which contain 1–5 carbon atoms; or aryl, which may be further substituted, one or more times, by alkyl or alkoxy, the alkyl portions of which have less than 5 carbon atoms; or combinations thereof.

18. A dye-conjugate, as claimed in claim 17, wherein the protein is an antibody, avidin, or streptavidin.

19. A dye-conjugate, as claimed in claim 17, wherein $R_3$ is a heteroaryl group; $R_2$ and $R_6$, which may be the same or different, are sulfo or a sodium salt thereof, hydrogen, or alkyl; and the remaining substituents, which may be the same or different, are hydrogen or alkyl.

20. A dye-conjugate, as claimed in claim 17, wherein $R_3$ is an alkenyl; $R_2$ and $R_6$, which may be the same or different, are sulfo or a sodium salt thereof, hydrogen, or alkyl; and the remaining substituents, which may be the same or different, are hydrogen or alkyl.

* * * * *

UNITED STATES PATENT AND TRADEMARK OFFICE
CERTIFICATE OF CORRECTION

PATENT NO. : 5,451,663
DATED : September 19, 1995
INVENTOR(S) : Kang, et al.

It is certified that error appears in the above-indentified patent and that said Letters Patent is hereby corrected as shown below:

At column 8, line 13 "$(CH_2)_2$—$CO_2$" should be --$(CH_2)_2$—$CO_2H$--.

At column 11, line 1, please insert the following heading:

| Table 3 | | | | | |
|---|---|---|---|---|---|
| --Compound | M.P. (°C) | $\lambda^{Abs}_{max}$ (nm)* | $\lambda^{Em}_{max}$ (nm)* | $R_f$ | T.L.C. Solvent$^§$ |

At column 11, line 32 "A=" should be --§A=--.

At column 11, line 59 "0.2" should be --10.2--.

At column 13, line 40 "Quantum Yield (Φ)" should be --Quantum Yield (Φ)‡--

At column 13, line 40 "Photostability" should be --Photostability§--.

At column 13, line 44 "R" should be --R†--.

At column 13, line 51 "NAOH" should be --NaOH--.

At column 13, line 55 "197 1" should be --1971--.

UNITED STATES PATENT AND TRADEMARK OFFICE
CERTIFICATE OF CORRECTION

PATENT NO. : 5,451,663
DATED : September 19, 1995
INVENTOR(S) : Kang, et al.

It is certified that error appears in the above-indentified patent and that said Letters Patent is hereby corrected as shown below:

At column 13, line 56 " Retention" should be --§ Retention--.

At column 26, line 20 "yesin" should be --resin--.

At column 26, line 28 "Ohio" should be --Ohio)--.

Signed and Sealed this

Eighth Day of September, 1998

*Attest:*

BRUCE LEHMAN

*Attesting Officer*    *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 bases
        ( B ) TYPE: Nucleic Acid
        ( C ) STRANDEDNESS: Single
        ( D ) TOPOLOGY: Linear ( i i ) MOLECULE TYPE: Other nucleic acid
        ( A ) DESCRIPTION: A 5'-amine- derivatized oligonucleotide prepared by automated solid phase synthesis.

( i i i ) HYPOTHETICAL: no ( i v ) ANTI-SENSE: no ( x i ) SEQUENCE DESCRIPTION: SEQ ID NO:1:

TGTAAAACGA CGGCCAGT                      18

( 2 ) INFORMATION FOR SEQ ID NO:2:

( i ) SEQUENCE CHARACTERISTICS:
        ( A ) LENGTH: 6 amino acids
        ( B ) TYPE: Amino Acid
        ( C ) STRANDEDNESS:
        ( D ) TOPOLOGY: Linear ( i i ) MOLECULE TYPE: Peptide ( i i i ) HYPOTHETICAL: no ( i x ) FEATURE:
        ( D ) OTHER INFORMATION: The Xaa in location 1 is N-formyl norleucine. The Xaa in position 4 is Norleucine (Nle)

( x i ) SEQUENCE DESCRIPTION: SEQ ID NO:2:

Xaa  Leu  Phe  Xaa  Tyr  Lys
1                        5